United States Patent
Campean et al.

(10) Patent No.: US 10,603,492 B2
(45) Date of Patent: Mar. 31, 2020

(54) SYSTEM, METHOD, AND APPARATUS FOR APPLYING TRANSCUTANEOUS ELECTRICAL STIMULATION

(71) Applicant: VERESSA MEDICAL, INC., Columbus, OH (US)

(72) Inventors: Alexandru Campean, Strongsville, OH (US); Jeff A. Weisgarber, Jewett, OH (US); Mingming Zhang, Hilliard, OH (US)

(73) Assignee: AVATION MEDICAL, INC., Columbus, OH (US)

(*) Notice: Subject to any disclaimer, the term of this patent is extended or adjusted under 35 U.S.C. 154(b) by 0 days.

(21) Appl. No.: 16/295,253

(22) Filed: Mar. 7, 2019

(65) Prior Publication Data
US 2020/0069943 A1    Mar. 5, 2020

Related U.S. Application Data

(60) Provisional application No. 62/751,173, filed on Oct. 26, 2018, provisional application No. 62/725,755, filed on Aug. 31, 2018.

(51) Int. Cl.
| | |
|---|---|
| *A61N 1/36* | (2006.01) |
| *A61B 5/0488* | (2006.01) |
| *A61B 5/00* | (2006.01) |
| *A61N 1/04* | (2006.01) |
| *A61B 5/053* | (2006.01) |

(52) U.S. Cl.
CPC ........ *A61N 1/36031* (2017.08); *A61B 5/0488* (2013.01); *A61B 5/053* (2013.01); *A61B 5/7221* (2013.01); *A61N 1/0456* (2013.01); *A61N 1/0484* (2013.01); *A61N 1/36007* (2013.01); *A61N 1/36021* (2013.01)

(58) Field of Classification Search
CPC .......................... A61N 1/36031; A61N 1/0456
USPC ......................................................... 607/41
See application file for complete search history.

(56) References Cited

U.S. PATENT DOCUMENTS

| | | |
|---|---|---|
| 5,871,534 A | 2/1999 | Messick et al. |
| 7,228,179 B2 | 6/2007 | Campen et al. |
| 7,742,823 B2 | 6/2010 | King et al. |
| 8,108,049 B2 | 1/2012 | King |
| 8,145,318 B2 | 3/2012 | Van Herk |
| 8,175,718 B2 | 5/2012 | Wahlgren et al. |
| 8,364,257 B2 | 1/2013 | Van Den Eerenbeemd et al. |
| 8,452,409 B2 | 5/2013 | Bachinski et al. |
| 8,620,434 B2 | 12/2013 | Bodlaender et al. |
| 8,626,312 B2 | 1/2014 | King et al. |
| 8,768,473 B2 | 7/2014 | Bachinski et al. |
| 8,792,991 B2 | 7/2014 | Gerber et al. |
| 8,862,238 B2 | 10/2014 | Rahimi et al. |
| 8,909,334 B2 | 12/2014 | Kolen et al. |
| 8,918,184 B1 | 12/2014 | Torgerson et al. |

(Continued)

*Primary Examiner* — Nadia A Mahmood
(74) *Attorney, Agent, or Firm* — Tarolli, Sundheim, Covell & Tummino LLP

(57) ABSTRACT

A system, method, and apparatus for treating a medical condition by applying transcutaneous electrical stimulation to a target peripheral nerve of a subject. Electrical stimulation is applied to the peripheral nerve via a stimulation electrode pattern under closed-loop control in which EMG responses are monitored and used to adjust stimulation parameters. In response to detecting an unacceptable recording, electrical stimulation is applied to the peripheral nerve under open-loop control.

16 Claims, 13 Drawing Sheets

(56) References Cited

U.S. PATENT DOCUMENTS

| | | |
|---|---|---|
| 8,948,876 B2 | 2/2015 | Gozani et al. |
| 8,958,886 B2 | 2/2015 | Schepis et al. |
| 9,002,477 B2 | 4/2015 | Burnett |
| 9,044,587 B2 | 6/2015 | Bachinski et al. |
| 9,084,897 B2 | 7/2015 | Yonce |
| 9,089,706 B2 | 7/2015 | King et al. |
| 9,114,261 B2 | 8/2015 | Yonce |
| 9,155,899 B2 | 10/2015 | Mashiach et al. |
| 9,220,895 B2 | 12/2015 | Siff et al. |
| 9,242,085 B2 | 1/2016 | Hershey et al. |
| 9,242,091 B2 | 1/2016 | Bachinski et al. |
| 9,254,382 B2 | 2/2016 | Ahmad et al. |
| 9,265,927 B2 | 2/2016 | Yonce et al. |
| 9,339,641 B2 | 5/2016 | Rajguru et al. |
| 9,387,338 B2 | 7/2016 | Burnett |
| 9,474,898 B2 | 10/2016 | Gozani et al. |
| 9,533,155 B2 | 1/2017 | Jiang et al. |
| 9,545,521 B1 | 1/2017 | Torgerson et al. |
| 9,555,246 B2 | 1/2017 | Jiang et al. |
| 9,572,708 B2 | 2/2017 | Petitt |
| 9,610,442 B2 | 4/2017 | Yoo et al. |
| 9,643,022 B2 | 5/2017 | Mashiach et al. |
| 9,662,491 B2 | 5/2017 | Yonce et al. |
| 9,675,801 B2 | 6/2017 | Kong et al. |
| 9,713,711 B2 | 7/2017 | Hershey et al. |
| 9,757,554 B2 | 9/2017 | Dar et al. |
| 9,770,595 B2 | 9/2017 | Yonce |
| 9,855,423 B2 | 1/2018 | Jiang et al. |
| 9,884,187 B2 | 2/2018 | Yoo et al. |
| 9,895,533 B2 | 2/2018 | Harpak et al. |
| 10,016,600 B2 | 7/2018 | Creasey et al. |
| 10,124,161 B2 | 11/2018 | Barker |
| 10,130,810 B2 | 11/2018 | Ferree et al. |
| 10,159,835 B2 | 12/2018 | Gozani et al. |
| 10,232,174 B2 | 3/2019 | Simon et al. |
| 2012/0302821 A1 | 11/2012 | Burnett |
| 2016/0045746 A1 | 2/2016 | Jiang et al. |
| 2016/0045747 A1 | 2/2016 | Jiang et al. |
| 2016/0114167 A1 | 4/2016 | Jiang et al. |
| 2016/0121123 A1 | 5/2016 | Jiang et al. |
| 2017/0361093 A1 | 12/2017 | Yoo et al. |

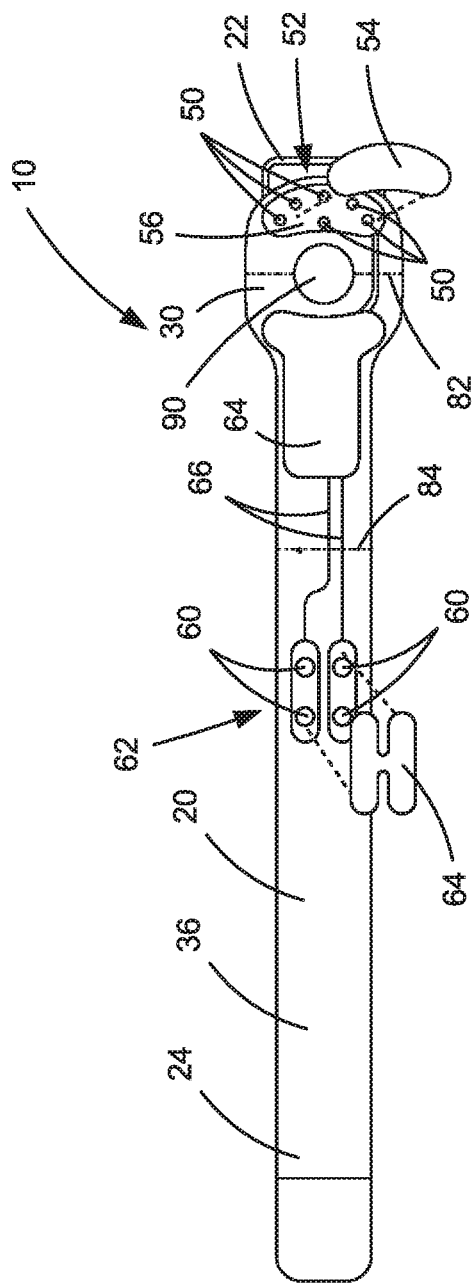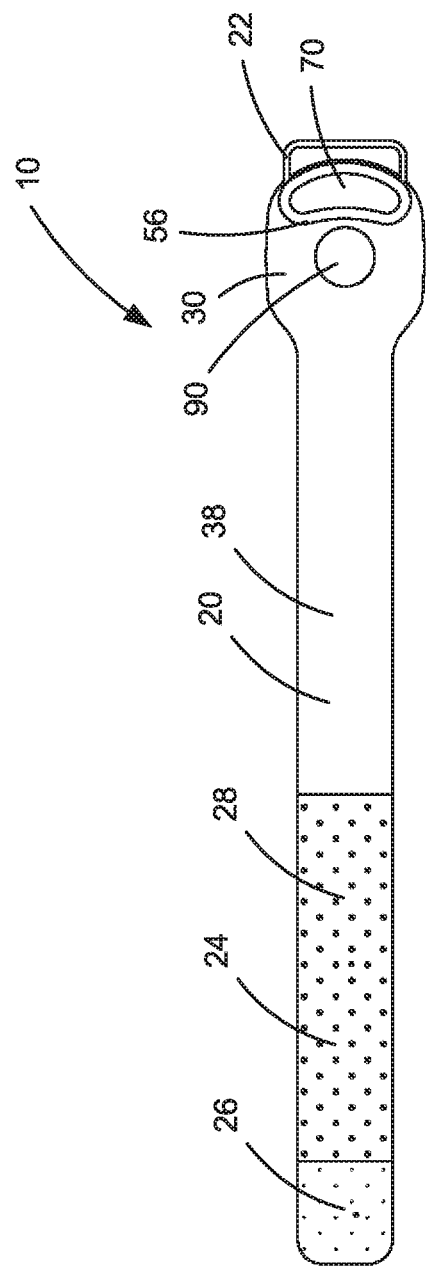

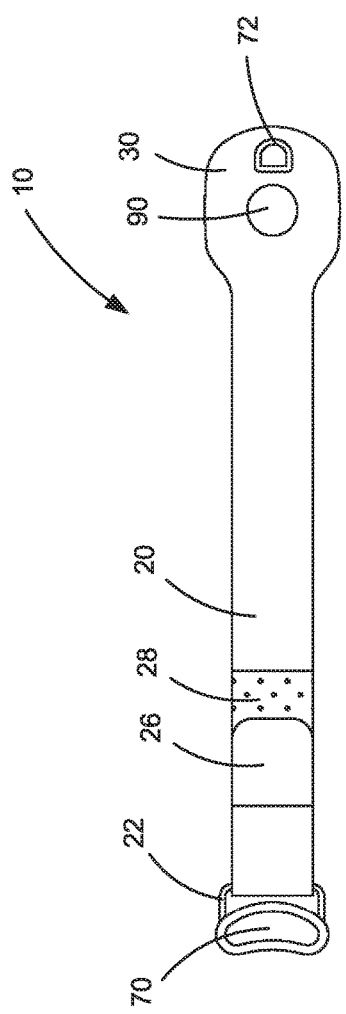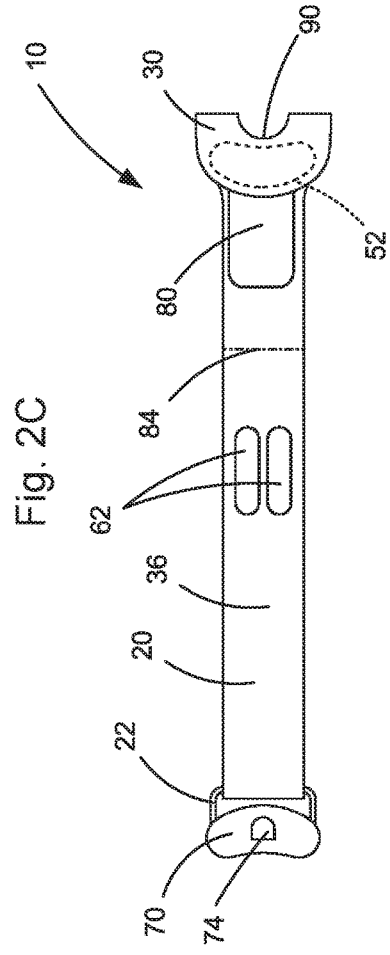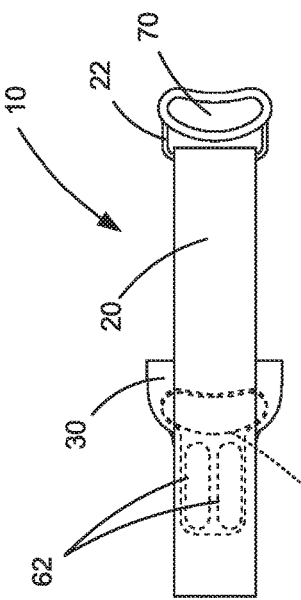

| Electrode | E1 | E2 | E3 | E4 | E5 | E6 | E7 | E8 |
|---|---|---|---|---|---|---|---|---|
| High Impedance? | N | N | N | N | N | Y | N | N |
| Pattern 1 | C | C | A | A | | | | |
| Pattern 2 | | C | A | A | A | | | |
| Pattern 3 | C | C | A | | | A | | |
| Pattern 4 | C | C | | A | | | | |
| Pattern 5 | | | | | A | | | C |
| Pattern 6 | | | | A | A | A | C | C |
| Pattern 7 | | | A | | A | A | C | C |
| Pattern 8 | | | | | | A | C | C |
| Pattern 9 | | | | | | A | C | C |
| Pattern 10 | | | | | A | | C | C |

SYSTEM, METHOD, AND APPARATUS FOR APPLYING TRANSCUTANEOUS ELECTRICAL STIMULATION

RELATED APPLICATIONS

This application claims the benefit of U.S. Provisional Application Ser. No. 62/725,755, filed on Aug. 31, 2018. This application also claims the benefit of U.S. Provisional Application Ser. No. 62/751,173, filed on Oct. 26, 2018. The subject matter of these applications is hereby incorporated by reference in its entirety.

TECHNICAL FIELD

The invention relates to a wearable electronic medical device for transcutaneous electrical stimulation of peripheral nerves for the purpose of treating one or more medical conditions.

BACKGROUND

There are many known technologies that use electrical stimulation of peripheral nerves to treat medical conditions. Implantable stimulation technologies require surgical implantation of stimulation leads, with a pulse generator that is either surgically implanted or connected externally to wire leads. Percutaneous stimulation technologies are less invasive, but still require the stimulation electrodes to pierce the skin. While these technologies can be effective in treating certain conditions, they are less desirable due to their invasiveness and because they can require the continued or routine attention of specialists, requiring doctor's office visits, phone calls, etc.

SUMMARY

A system for applying transcutaneous electrical stimulation includes a wearable, such as a garment, sock, sleeve, brace, strap, etc. The wearable includes an electronic stimulator device that provides transcutaneous electrical stimulation to peripheral nerves for treatment of medical conditions. Advantageously, the wearable allows the subject to use the system at a time and place that is convenient. The subject may choose to use the device while they are at work or at home, or while walking, relaxing, or sleeping, as long as certain environments and/or activities (e.g., wet environments/activities) are avoided. Since there are no implantable or percutaneous components, the risk of infection, battery fault burns, and transcutaneous power transfer discomfort and/or bleeding, are greatly reduced or eliminated.

The wearable includes electrodes that are arranged in a predetermined pattern or array, and that engage the subject's skin at desired locations when the wearable is worn. These skin surface mounted electrodes can, for example, be similar to those of other transcutaneous electrical nerve stimulation ("TENS") units to implement high voltage skin surface electrical stimulation. The electrodes include stimulating electrodes and recording electrodes, which the wearable can position at the same location or at different locations on the subject's skin. In fact, the identities of individual electrodes, i.e., stimulating or recording, can change depending on the application/treatment for which the system is being used. The stimulating electrodes apply the transcutaneous electrical stimulation to the subject's skin, and the recording electrodes record the electromyogram (EMG) responses elicited by the stimulation.

The wearable also includes a control unit that is electrically connected to the electrodes and that is operable to control electrical stimulation applied by the stimulating electrodes and to control the recording of EMG responses by the recording electrodes. The control unit executes closed-loop control algorithms, which adjust stimulation patterns, periodically or constantly, based on the elicited EMG response from the recruited nerves as feedback. Alternatively, instead of the EMG response providing the closed-loop feedback, or as a supplement to the EMG response, the system can include alternative devices, such as mechanomyogram (MMG) devices (e.g., an accelerometer), or can implement electronic measurements, such as electrode impedance, to implement the closed-loop control.

This closed-loop control eliminates the need for "programming sessions" commonly required for neurostimulation systems. The day-to-day variability that arises due to electrode placement and skin impedance necessitates these sessions to make sure that the electrodes are positioned to provide adequate stimulation treatment. With the present system, instead of physically adjusting the electrode positions on the subject in order to find the arrangement that produces the desired response, the system itself can select which electrodes to use, and can adjust the number and pattern of electrodes until an acceptable response (EMG and/or MMG) is achieved. Once the appropriate electrodes pattern is identified, the order, intensity, timing, etc. of the stimulation can be further tuned or adjusted to optimize the EMG and/or MMG response. The system can tailor the electrical stimulation applied by each individually controllable electrode in the array so that the stimulation characteristics of each electrode (e.g., frequency, amplitude, pattern, duration, etc.) is configured to deliver the desired stimulation effect. This tailoring can be implemented automatically through the algorithm, which incrementally adjusts these characteristics, monitoring the and/or response at each increment until optimal settings are identified. Stimulation therapy can then be applied with these settings, according to the algorithm, which can be dictated by the requirements of the treating physician.

Throughout the electrical stimulation treatment process, the system can implement periodic or continuous measurement of system integrity. One such measurement is that of electrode impedance to remove the risks that can arise when electrodes lift away from the skin or certain properties of the electrodes deteriorate. The impedance measurement capability could also potentially be used to provide an indication of the optimal electrode location for nerve stimulation. This may be the case, for example, in areas where the skin is thin and where the stimulated nerves are most superficial. Thus, impedance values may be used as an input to the closed-loop stimulation algorithm to adjust stimulation patterns. By way of example, when stimulating the tibial nerve, the posterior area of the medial malleolus typically has comparatively thin skin and is the site where tibial nerve is most superficial, which leads to its being a good candidate for measuring electrode impedance.

The control unit and the architecture of the system may be designed to constantly optimize stimulation by monitoring the quality of nerve recruitment periodically or on a pulse-by-pulse basis, with the goal of keeping recruitment strength to a minimum (which can reduce muscle twitching) and to minimize the stimulation energy being delivered through the skin. The EMG recording feature is capable of detecting both M-wave and F-wave responses, which can be used as feedback inputs (together or independently) to the closed-loop stimulation algorithm to determine the level of activation of the stimulated peripheral nerve. A significant aspect of the F-wave is that it provides an indication that the stimulation-evoked peripheral nerve action potential has activated motor neurons in the associated spinal cord nerves/nerve plexus. For example, an F-wave response to tibial nerve stimulation indicates that the tibial nerve action potential has activated motor neurons in the sacral spinal cord/sacral plexus.

The wearable transcutaneous electrical stimulation device can be used to stimulate various peripheral nerves in order to treat medical conditions associated with those nerves. For example, the system can be used to apply electrical stimulation to the tibial nerve to treat pelvic floor dysfunction, e.g., overactive bladder (OAB) medical conditions. As another example, the system can be used to apply electrical stimulation to the tibial nerve to treat sexual dysfunction. In this manner, it is believed that tibial nerve stimulation could be used to treat genital arousal aspects of female sexual interest/arousal disorder by improving pelvic blood flow. In yet another example, the system can be used to apply electrical stimulation to the tibial nerve to treat plantar fasciitis.

As another example, the system can be applied to the wrist area to provide stimulation to the ulnar nerve and/or median nerve. The stimulation electrode array can, for example, be placed on the inside of the lower arm anywhere 0 to 20 cm from the wrist line, EMG recording electrodes can be placed on the base of thumb to record signal from abductor/flexor pollicis brevis. EMG recording electrodes alternatively or additionally can be placed on the base of pinky to record signal from abductor/flexor digiti minimi brevis. The nerve activation could be confirmed by recording M-wave and F-wave EMG signals from the relevant muscles. The EMG signal can also be used as a control signal to adjust the stimulation parameters or stimulation electrode patterns. This technology can be applied to median nerve activation for pain management in carpal tunnel syndrome, hypertension management, and nerve conduction study/nerve injury diagnosis for median/ulnar nerve neuropathy, etc.

As a further example, the system can be used to apply transcutaneous electrical stimulation to provide neurostimulation to peripheral nerves in order to enhance nerve regeneration after peripheral nerve injury.

Implementing closed-loop control, the system can utilize measured EMG responses to detect and obtain data related to the electrical activity of muscles in response to the applied stimulation. This data can be used as feedback to tailor the application of the electrical stimulation. Additionally or alternatively, the system can also implement MMG sensors, such as accelerometers, to measure the physical response of the muscles. Other feedback, such as impedance measurements between electrodes and other biopotential recording, can also be utilized. Through this closed-loop implementation, the system can utilize techniques such as current steering and nerve localization to provide peripheral nerve stimulation therapy for treating various medical conditions.

The system, method, and apparatus for applying transcutaneous electrical stimulation disclosed herein has many aspects, which can be included or utilized in various combinations.

According to one aspect, a method treats a medical condition by applying transcutaneous electrical stimulation to a target peripheral nerve of a subject.

According to another aspect, alone or in combination with any other aspect, the method can include positioning a plurality of stimulation electrodes on a skin surface proximate the targeted peripheral nerve, the stimulation electrodes being spaced from each other in a predetermined configuration. The method also can include positioning one or more recording electrodes on a skin surface remote from the stimulation electrodes at a location where electromyogram (EMG) responses to electrical stimulation of the targeted peripheral nerve can be detected. The method also can include stimulating the peripheral nerve by applying electrical stimulation pulses via a stimulation electrode pattern selected from the plurality of stimulation electrodes according to stimulation parameters under closed-loop control in which EMG responses to the electrical stimulation pulses are monitored via the recording electrodes and the stimulation parameters are adjusted in response to the monitored EMG responses. The method further can include, in response to detecting an unacceptable condition of the recording electrodes, applying electrical stimulation pulses via the stimulation electrode pattern according to the stimulation parameters under open-loop control in which the stimulation parameters are maintained without adjustment.

According to another aspect, alone or in combination with any other aspect, the unacceptable condition of the recording electrodes can include unacceptable impedance measurements.

According to another aspect, alone or in combination with any other aspect, the step of applying electrical stimulation pulses further can include monitoring for mechanomyogram (MMG) responses to the electrical stimulation pulses and applying the electrical stimulation pulses under closed-loop control in which the stimulation parameters are adjusted in response to the monitored MMG responses.

According to another aspect, alone or in combination with any other aspect, the step of applying electrical stimulation pulses can include detecting impedances of the recording electrodes and, in response to detecting acceptable impedances of the recording electrodes, applying the electrical stimulation pulses.

According to another aspect, alone or in combination with any other aspect, the method can include: obtaining sample measurements via the recording electrodes, checking the sample measurements for noise, checking the sample measurements for voluntary EMG responses, applying the electrical stimulation pulses under closed-loop control in response to determining an acceptable level of noise and the absence of voluntary EMG responses, and applying the electrical stimulation pulses under open-loop control in response to determining an unacceptable level of noise or the presence of voluntary EMG responses.

According to another aspect, alone or in combination with any other aspect, each application of an electrical stimulation pulse under closed-loop control can include: applying the electrical stimulation pulse, executing a time delay, recording EMG responses via the recording electrodes after the time delay is executed, and adjusting the stimulation parameters in response to the recorded EMG responses. The duration of the time delay can be about 5 ms or less.

According to another aspect, alone or in combination with any other aspect, adjusting the stimulation parameters in response to the recorded EMG responses under closed loop control can include: increasing the amplitude of subsequent stimulation pulses in response to the recorded EMG responses being below a predetermined EMG window, decreasing the amplitude of subsequent stimulation pulses in response to the recorded EMG responses being above the predetermined EMG window, and maintaining the amplitude of subsequent stimulation pulses in response to the recorded EMG responses being within the predetermined EMG window.

According to another aspect, alone or in combination with any other aspect, each application of an electrical stimulation pulse under open-loop control can include: applying the electrical stimulation pulse, and executing a time delay having a duration sufficient to maintain a constant stimulation period. The duration of the time delay can be about 75 ms.

According to another aspect, alone or in combination with any other aspect, the stimulation electrode pattern can be selected from a pattern list, wherein the method further can further include generating the pattern list by:
 a) identifying a set of predetermined stimulation electrode patterns, each stimulation electrode pattern identifying which of the plurality of stimulation electrodes will apply the electrical stimulation pulses, and each stimulation electrode pattern having associated with it the stimulation parameters according to which it applies stimulation pulses;
 b) selecting a stimulation electrode pattern from the set of predetermined stimulation electrode patterns;
 c) generating a stimulation pulse using the selected stimulation electrode pattern according to its associated stimulation parameters;
 d) determining via the recording electrodes whether the stimulation pulse using the selected stimulation electrode pattern elicited an EMG response;
 e) adding the selected stimulation electrode pattern to the pattern list in response to detecting an EMG response;
 f) omitting the selected stimulation electrode pattern from the pattern list in response to not detecting an EMG response; and
 repeating steps b) through f) for each stimulation electrode pattern in the set of predetermined stimulation electrode patterns to complete the pattern list.

According to another aspect, alone or in combination with any other aspect, the method can include optimizing the stimulation electrode patterns in the pattern list by:
 g) adjusting the stimulation parameters for each stimulation electrode pattern in the pattern list to attempt to elicit an improved EMG response;
 h) selecting a stimulation electrode pattern from the set of predetermined stimulation electrode patterns;
 i) generating a stimulation pulse using the selected stimulation electrode pattern according to its associated stimulation parameters;
 j) determining via the recording electrodes whether the stimulation pulse using the selected stimulation electrode pattern elicited an EMG response;
 k) adding the selected stimulation electrode pattern to the pattern list in response to detecting an EMG response;
 l) omitting the selected stimulation electrode pattern from the pattern list in response to not detecting an EMG response; and
 repeating steps h) through l) for each stimulation electrode pattern in the set of predetermined stimulation electrode patterns to complete the pattern list. Steps h) through l) can be repeated until each electrode pattern in the pattern list is optimized.

According to another aspect, alone or in combination with any other aspect, the method can also include ordering the stimulation electrode patterns in the pattern list according to their elicited EMG and/or MMG responses.

According to another aspect, alone or in combination with any other aspect, stimulating the peripheral nerve can include stimulating the tibial nerve. Stimulating the peripheral nerve can include stimulating the tibial nerve at a location between the medial malleolus and the Achilles tendon.

According to another aspect, alone or in combination with any other aspect, monitoring EMG responses can include recording EMG signals that result from recruitment of the tibial nerve's motor fibers. This can include positioning the recording electrodes on the bottom of the subject's foot near the abductor hallucis and the flexor hallucis brevis to record the EMG signals.

According to another aspect, alone or in combination with any other aspect, stimulating the peripheral nerve can treat overactive bladder, sexual dysfunction, or plantar fasciitis.

According to another aspect, alone or in combination with any other aspect, stimulating the peripheral nerve can include stimulating the ulnar nerve and/or median nerve for pain management in carpal tunnel syndrome, hypertension management, and nerve conduction study/nerve injury diagnosis for median/ulnar nerve neuropathy, etc. Stimulating the ulnar nerve and/or median nerve can treat carpal tunnel syndrome or hypertension. Stimulating the ulnar nerve and/or median nerve to perform a nerve conduction study or nerve injury diagnosis.

According to another aspect, alone or in combination with any other aspect, stimulating the ulnar nerve and/or median nerve can include positioning the stimulating electrodes on the inside of the lower arm 0 to 20 cm from the wrist line, and recording EMG responses can include positioning the recording electrodes on the base of thumb to record signal from abductor/flexor pollicis brevis, and/or positioning the recording electrodes on the base of pinky to record signal from abductor/flexor digiti minimi brevis.

According to another aspect, alone or in combination with any other aspect, stimulating the peripheral nerve can include applying the electrical stimulation pulses to the peripheral nerve to enhance nerve regeneration after peripheral nerve injury.

According to another aspect, alone or in combination with any other aspect, a system for treating overactive bladder by applying transcutaneous electrical stimulation to the tibial nerve of a subject can include a plurality of electrical stimulation electrodes, the stimulation electrodes being spaced from each other in a predetermined configuration, one or more recording electrodes, a structure for supporting the stimulation electrodes and the recording electrodes spaced apart from each other, and a control unit for controlling the operation of the stimulation electrodes and the recording electrodes. The control unit can be configured to perform the method according to any of the aspects disclosed herein, alone or in combination with any other aspect.

According to another aspect, alone or in combination with any other aspect, an apparatus for applying electrical stimulation includes a plurality of electrical stimulation electrodes spaced from each other in a predetermined configuration, one or more recording electrodes, a structure for supporting the stimulation electrodes and the recording electrodes spaced apart from each other, and a control unit for controlling the operation of the stimulation electrodes and the recording electrodes. The control unit is configured to energize the stimulation electrodes under closed-loop control using the recording electrodes to measure feedback, energize the stimulation electrodes under open-loop without measuring feedback, and determine whether to energize the stimulation electrodes under closed-loop control or open-loop control based on determining whether the feedback measured by the recording electrodes is reliable.

According to another aspect, alone or in combination with any other aspect, the structure can include a wearable structure configured to position the stimulation electrodes in the proximity of a peripheral nerve and to position the recording electrodes in the proximity of a muscle activated by the peripheral nerve.

According to another aspect, alone or in combination with any other aspect, the wearable structure can position the stimulation electrodes proximate the peripheral nerve and the recording electrodes proximate a location where EMG signals that result from recruitment of the peripheral nerve's motor fibers can be detected.

According to another aspect, alone or in combination with any other aspect, the wearable structure can include a strap, wherein the stimulation electrodes and recording electrodes are positioned at different locations along the length of the strap. The strap can be configured to have a portion wrapped around the subject's ankle to position the stimulating electrodes proximate the tibial nerve between the medial malleolus and the Achilles tendon. The strap can also be configured to have a portion wrapped around the subject's foot to position the recording electrodes on the bottom of the subject's foot near the abductor hallucis and the flexor hallucis brevis.

According to another aspect, alone or in combination with any other aspect, the wearable structure can include a brace comprising an upper portion upon which the stimulation electrodes are positioned and a lower portion upon which the recording electrodes are positioned. The upper portion of the brace can be configured to be wrapped around the subject's ankle to position the stimulating electrodes proximate the tibial nerve between the medial malleolus and the Achilles tendon. The lower portion of the brace can be configured to be wrapped around the subject's foot to position the recording electrodes on the bottom of the subject's foot near the abductor hallucis and the flexor hallucis brevis.

According to another aspect, alone or in combination with any other aspect, the apparatus can also include an accelerometer supported by the support structure adjacent or near the recording electrodes, wherein the control unit can be configured to determine whether to energize the stimulation electrodes under closed-loop control or open-loop control based on acceleration values determined by the accelerometer.

According to another aspect, alone or in combination with any other aspect, the control unit can include a microcontroller, a stimulator output stage controlled by the microcontroller, and at least one analog output switch operatively connected to the stimulator output stage and controlled by the microcontroller. The stimulator output stage can include a plurality of channels for providing electrical current to the stimulating electrodes via the output switch, wherein each channel of the output stage includes a current source and current sink, and wherein the microcontroller is configured to actuate the output switch to selectively identify which stimulation electrodes are active and to assign a channel of the output stage with each active stimulation electrode, wherein the output stage associated with each stimulating electrode determines whether the stimulating electrode operates as an anode or a cathode.

According to another aspect, alone or in combination with any other aspect, the microcontroller can be configured to determine amplitude and timing values for the current source and current sink for each channel of the output stage and their associated active stimulation electrodes.

According to another aspect, alone or in combination with any other aspect, the apparatus can include an impedance measurement circuit that is operatively connected to the stimulator output stage and is configured to measure electrode impedances.

According to another aspect, alone or in combination with any other aspect, the apparatus can include at least one analog input switch that is operatively connected to the microcontroller, wherein the microcontroller is configured to operate the analog input switch to determine which of the recording electrodes are used to measure feedback.

According to another aspect, alone or in combination with any other aspect, the apparatus can include an analog front end circuit that is operatively connected to the analog input switch, wherein the analog front end is configured to facilitate sampling the recording electrodes at a predetermined sample rate in order to determine whether the feedback measured by the recording electrodes is reliable. The sample rate can be 1,000-8,000 samples per second.

According to another aspect, alone or in combination with any other aspect, the microcontroller can be configured to initiate via the analog front end a sampling window after energizing the stimulation electrodes, wherein during the sampling window the recording electrodes are used to measure feedback signals to determine whether EMG data is present.

According to another aspect, alone or in combination with any other aspect, the apparatus can include a radio for communicating wirelessly with an external device for programming the microcontroller, uploading/downloading data, and remotely monitoring and/or controlling operation of the control unit.

According to another aspect, alone or in combination with any other aspect, a method for treating overactive bladder can include applying transcutaneous electrical stimulation to the tibial nerve of a subject. The method can include positioning a plurality of stimulation electrodes on a skin surface at a location between the medial malleolus and the Achilles tendon proximate the tibial nerve, the stimulation electrodes being spaced from each other in a predetermined configuration. The method also can include positioning one or more recording electrodes on a skin surface remote from the stimulation electrodes at a location on the bottom of the subject's foot near the abductor hallucis and the flexor hallucis brevis muscles to record electromyogram (EMG) responses that result from recruitment of the tibial nerve's motor fibers. The method also can include stimulating the tibial nerve by applying electrical stimulation pulses via a stimulation electrode pattern selected from the plurality of stimulation electrodes according to stimulation parameters under closed-loop control in which EMG responses to the electrical stimulation pulses are monitored via the recording electrodes and the stimulation parameters are adjusted in response to the monitored EMG responses. The method further can include, in response to detecting an unacceptable condition of the recording electrodes, applying electrical stimulation pulses via the stimulation electrode pattern according to the stimulation parameters under open-loop control in which the stimulation parameters are maintained without adjustment.

According to another aspect, alone or in combination with any other aspect, a system for treating overactive bladder by applying transcutaneous electrical stimulation to the tibial nerve of a subject can include a plurality of electrical stimulation electrodes, the stimulation electrodes being spaced from each other in a predetermined configuration, one or more recording electrodes, a structure for supporting the stimulation electrodes and the recording electrodes spaced apart from each other, and a control unit for controlling the operation of the stimulation electrodes and the recording electrodes. The control unit can be configured to perform the method according to any of the aspects disclosed herein, alone or in combination with any other aspect.

DRAWINGS

FIG. 2A is an inner surface plan view of the electronic medical device of FIGS. 1A and 1B.

FIG. 2B is an outer surface plan view of the electronic medical device of FIGS. 1A and 1B.

Figure 1A:
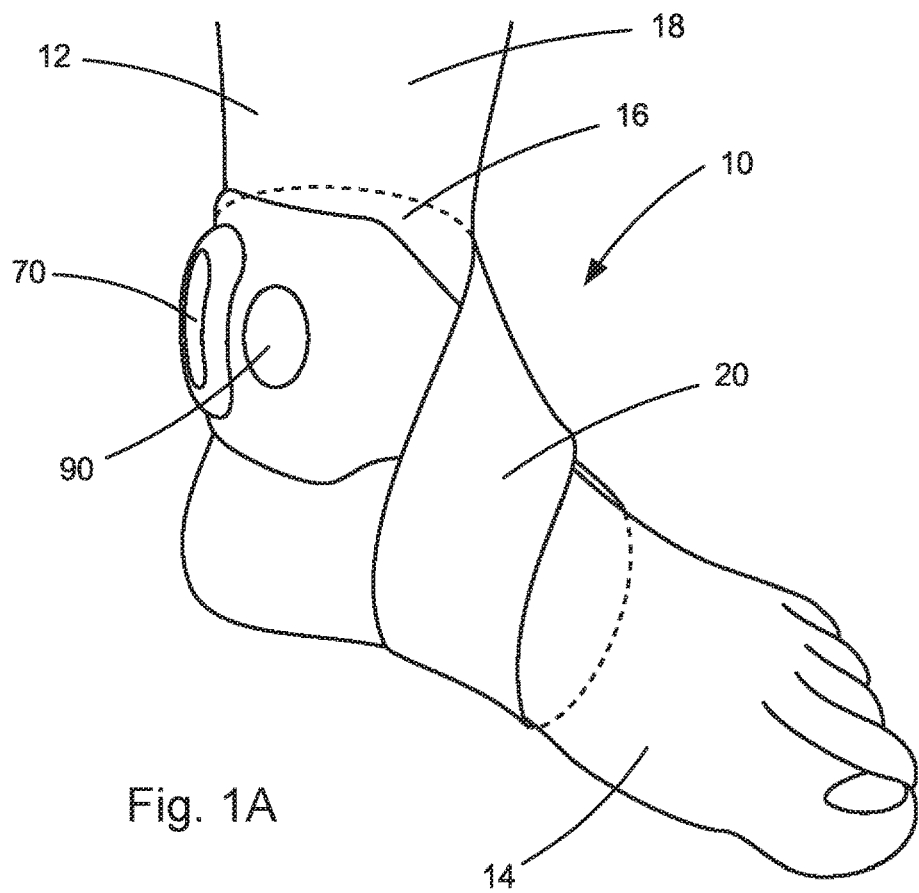
FIG. 1A illustrates a left-foot implementation of an electronic medical device for delivering transcutaneous electrical stimulation of peripheral nerves, according to a first example configuration.
Figure 1B:
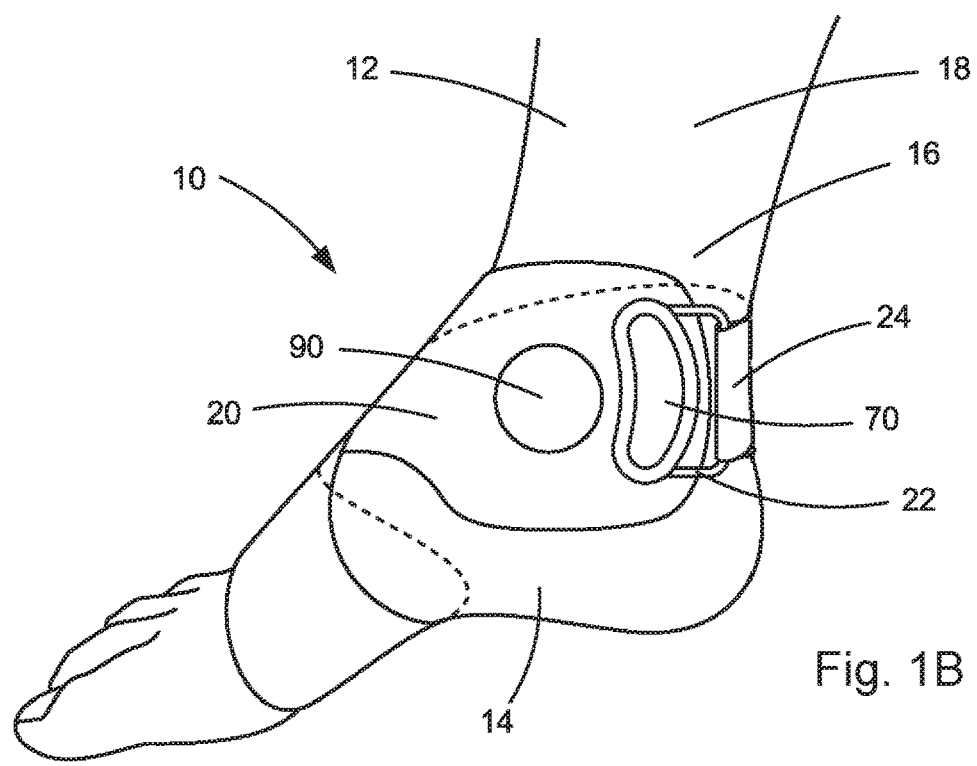
FIG. 1B illustrates a right-foot implementation of the electronic medical device for delivering transcutaneous electrical stimulation of peripheral nerves, according to the first example configuration.

FIGS. 2C-E are outer surface plan views of the electronic medical device of FIGS. 1A and 1B illustrating sequential steps in preparing the device for use.

Figure 3A:
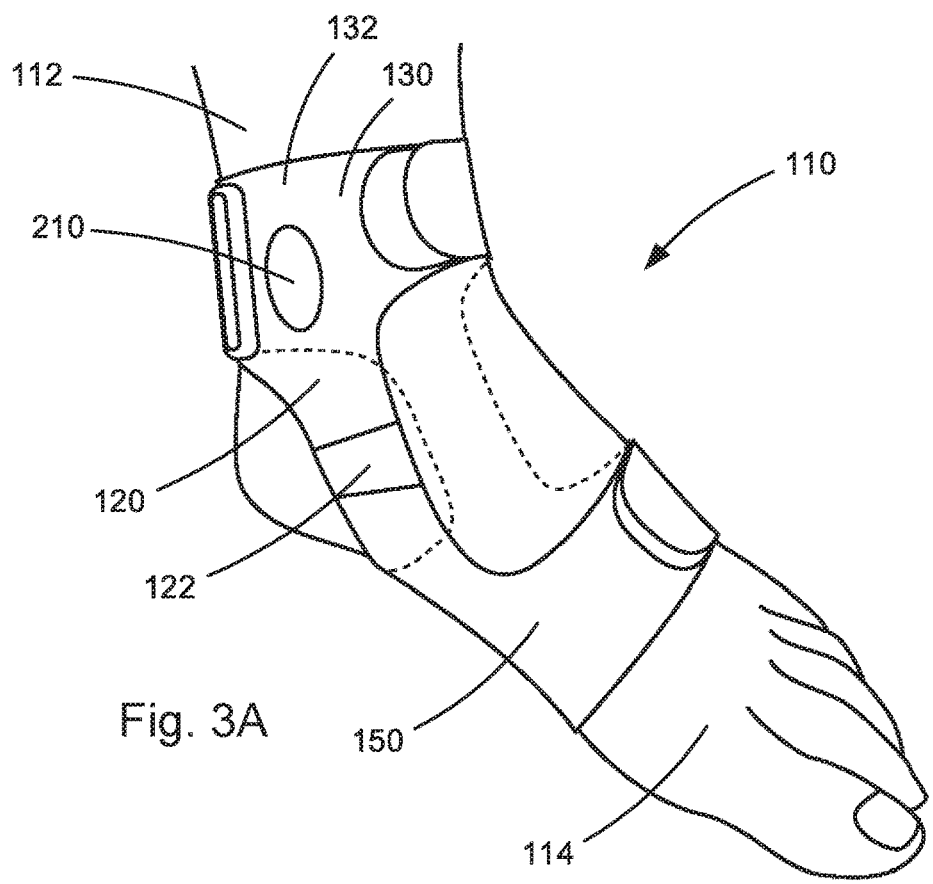

FIG. 3A illustrates a left-foot implementation of an electronic medical device for delivering transcutaneous electrical stimulation of peripheral nerves, according to a second example configuration.

Figure 3B:
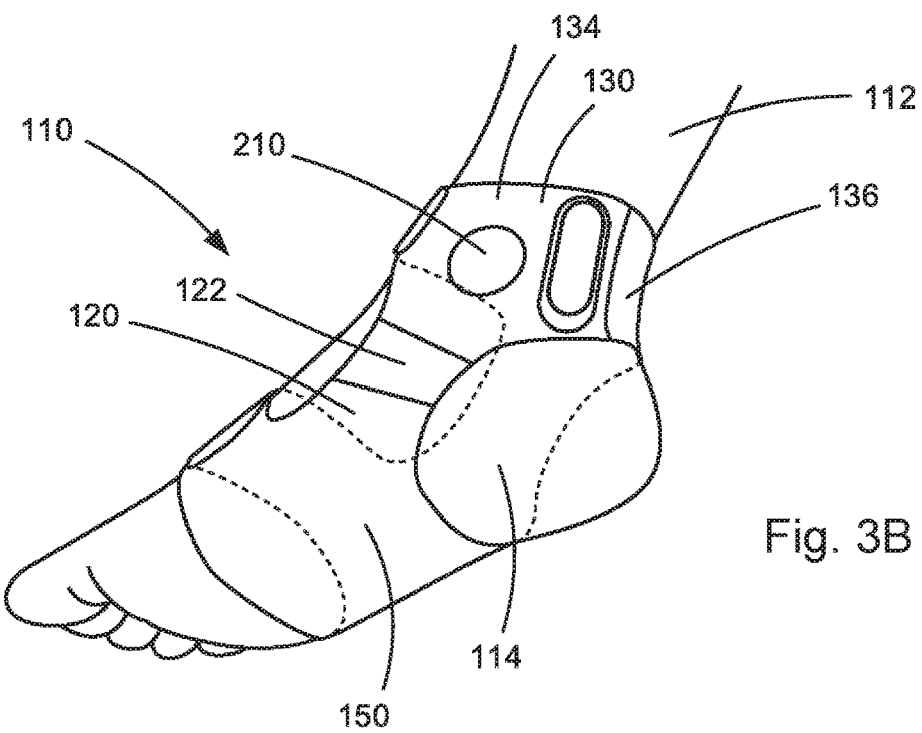

FIG. 3B illustrates a right-foot implementation of the electronic medical device for delivering transcutaneous electrical stimulation of peripheral nerves, according to the second example configuration.

Figure 4A:
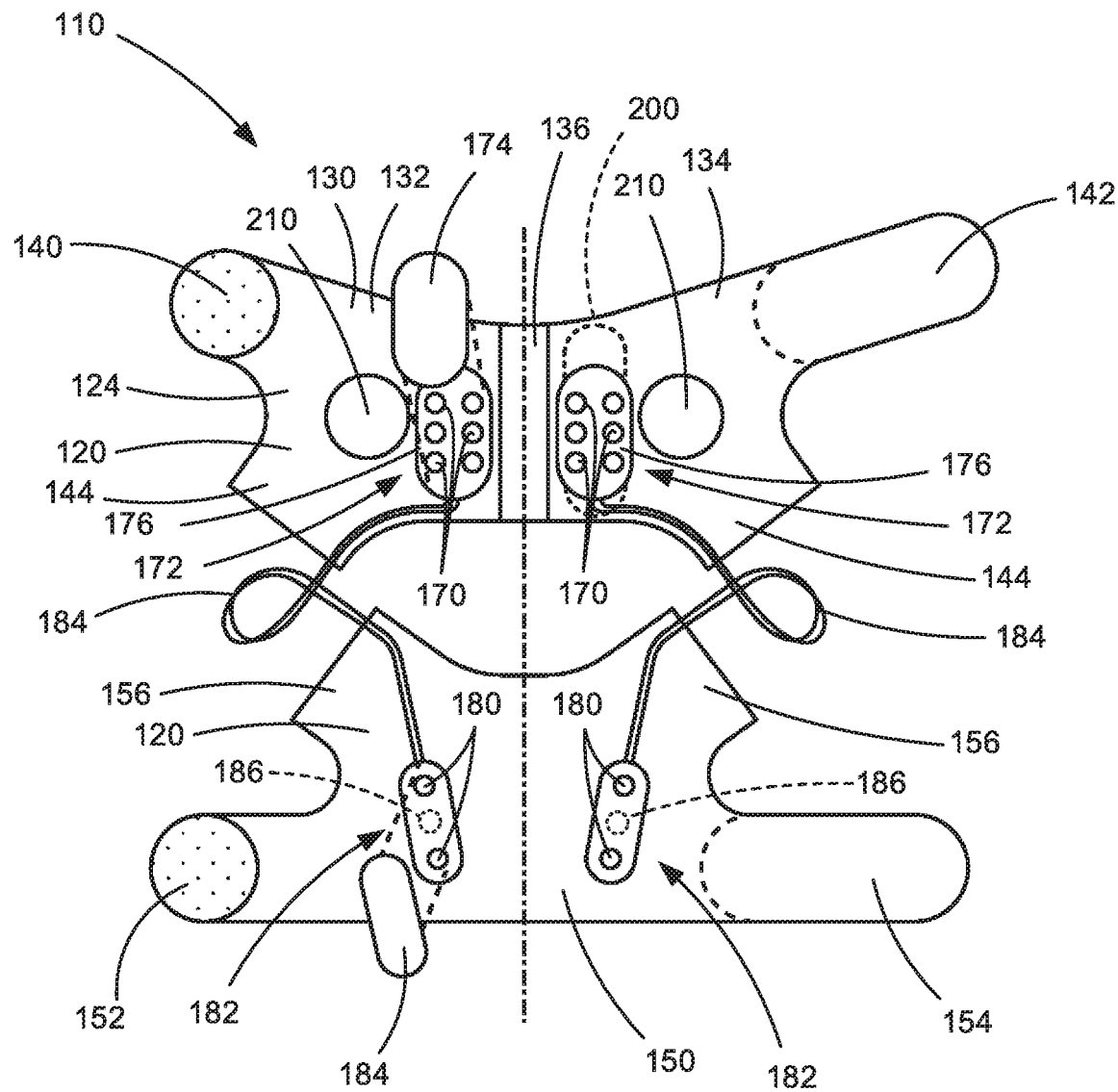

FIG. 4A is an inner surface plan view of components of the electronic medical device of FIGS. 3A and 3B.

Figure 4B:
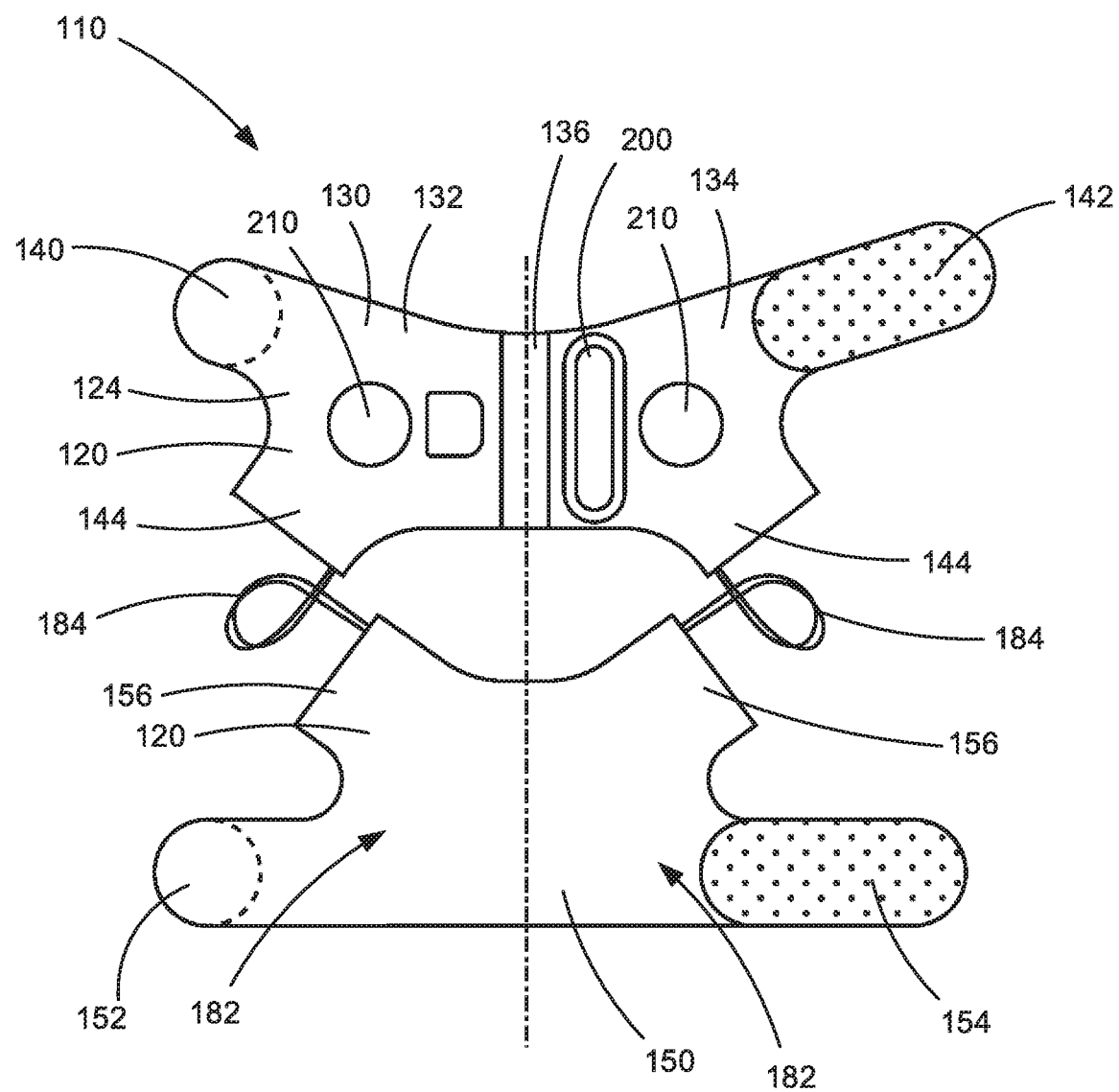

FIG. 4B is an outer surface plan view of the components of the electronic medical device of FIGS. 3A and 3B.

Figure 4C:
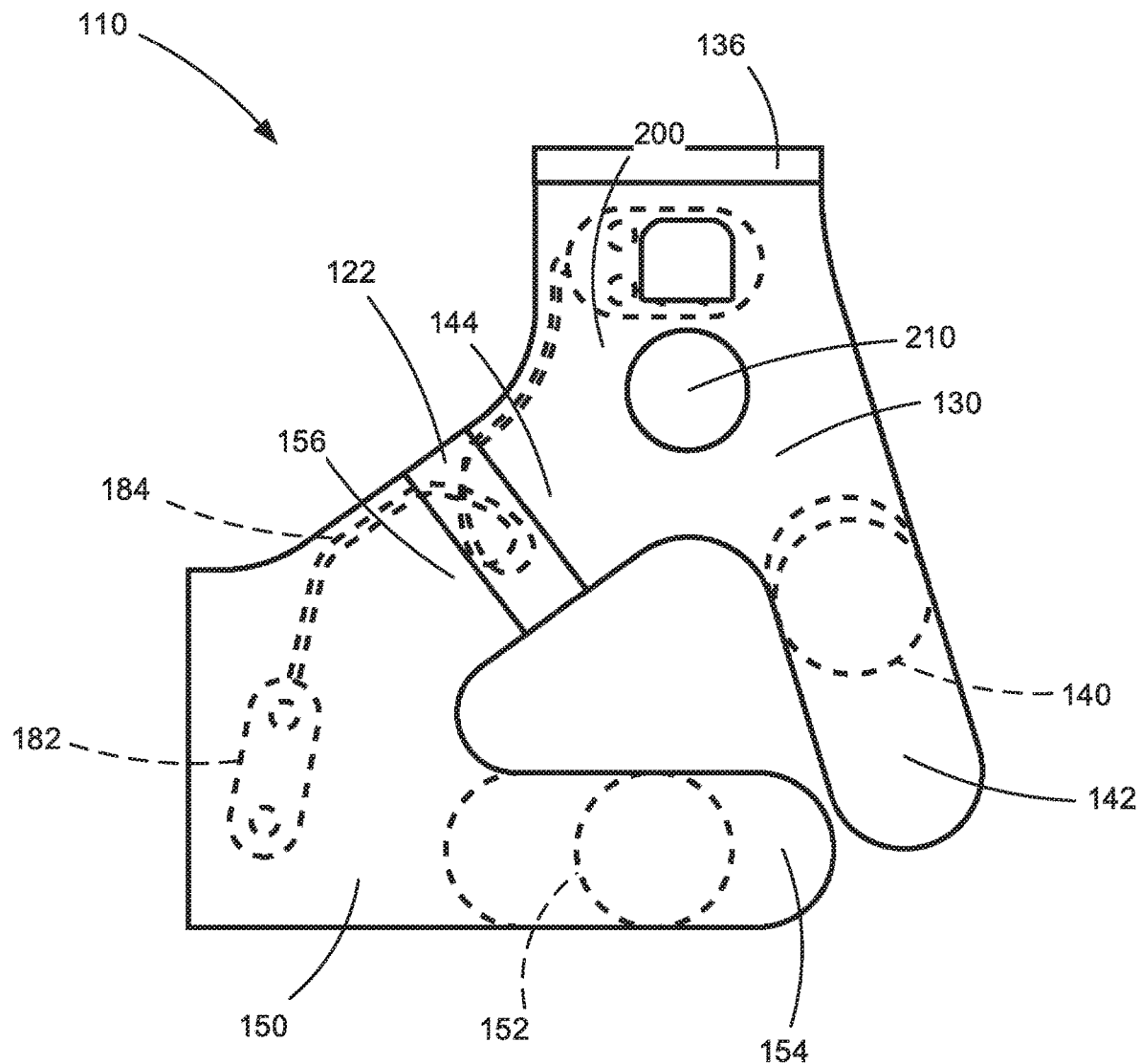

FIG. 4C is an outer surface plan view, taken from a first side, illustrating the components of FIGS. 4A and 4B assembled to form the electronic medical device of FIGS. 3A and 3B.

Figure 4D:
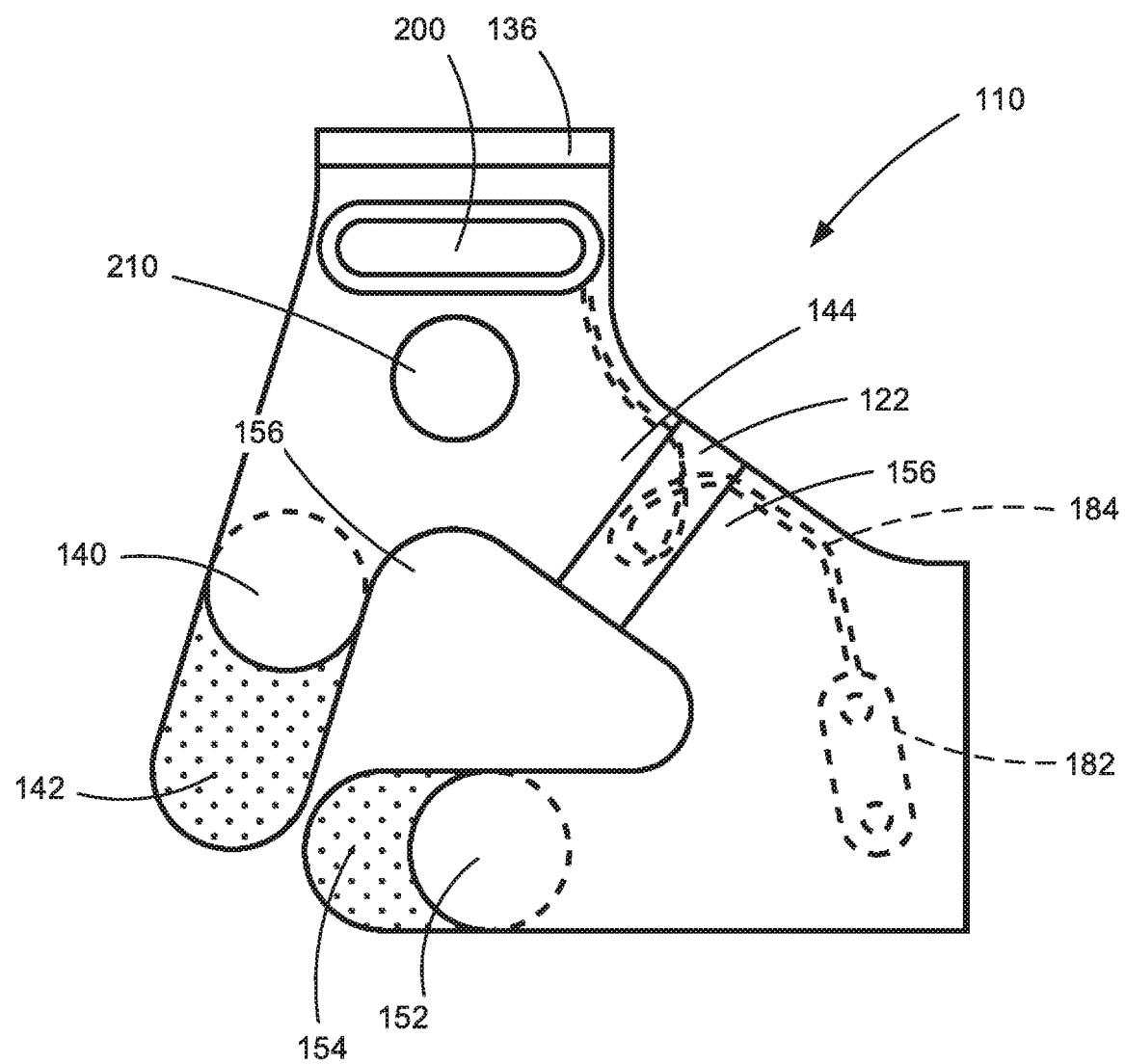

FIG. 4D is an outer surface plan view, taken from a second side, opposite the first side, illustrating the components of FIGS. 4A and 4B assembled to form the electronic medical device of FIGS. 3A and 3B.

Figure 5:
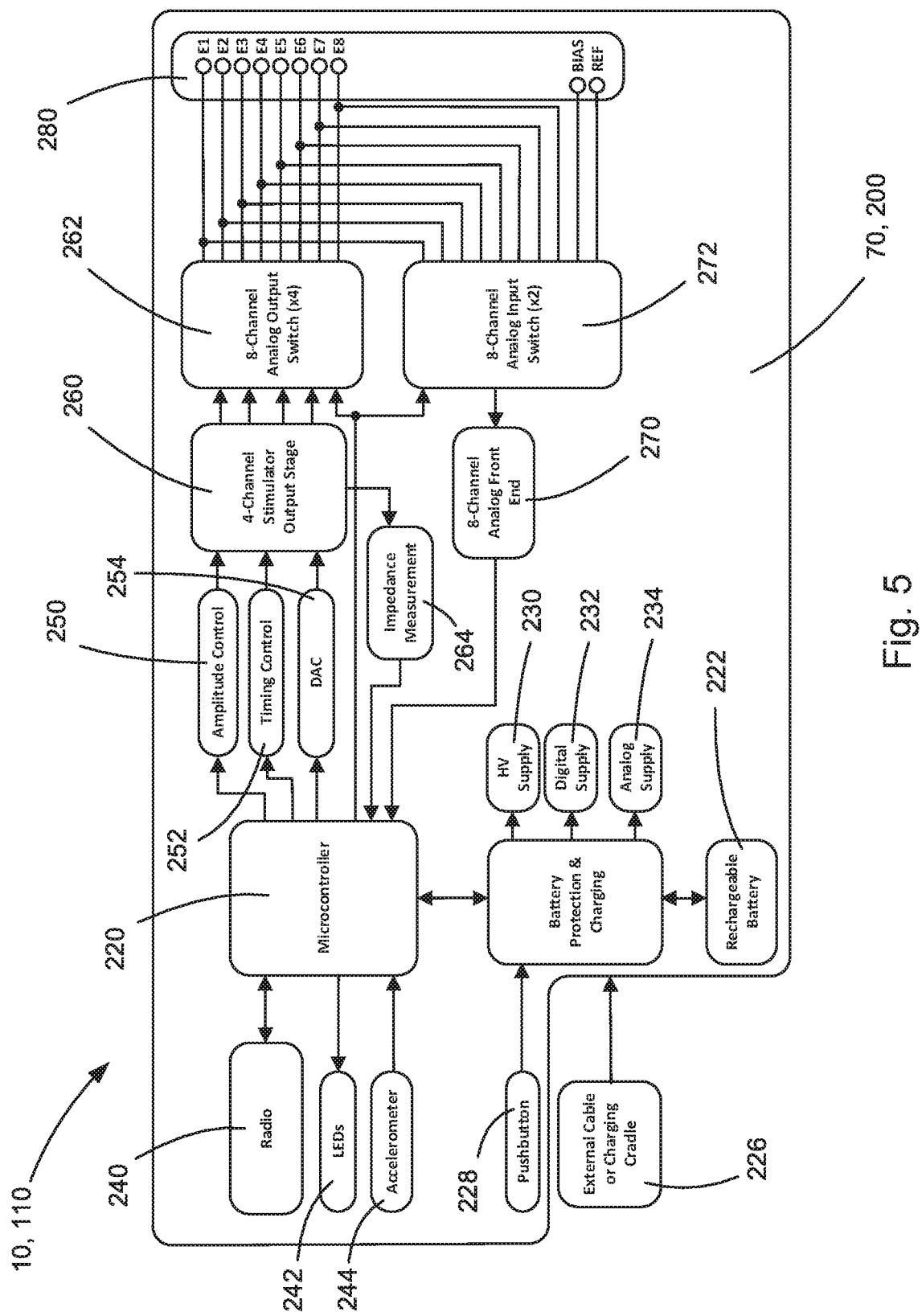

FIG. 5 is a schematic block diagram of a control unit portion of the electronic medical device.

Figure 6:
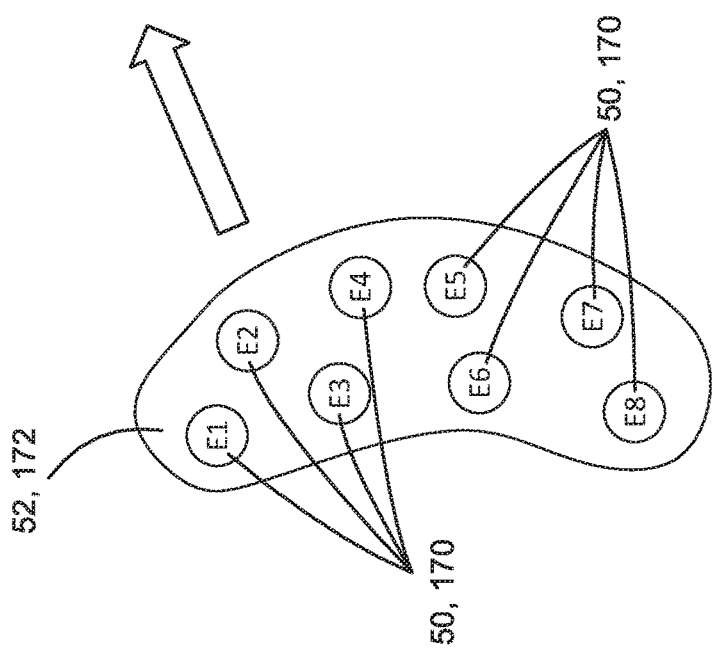

FIG. 6 is a diagram illustrating example electrode arrangements for portions of the electronic medical device.

Figure 7:
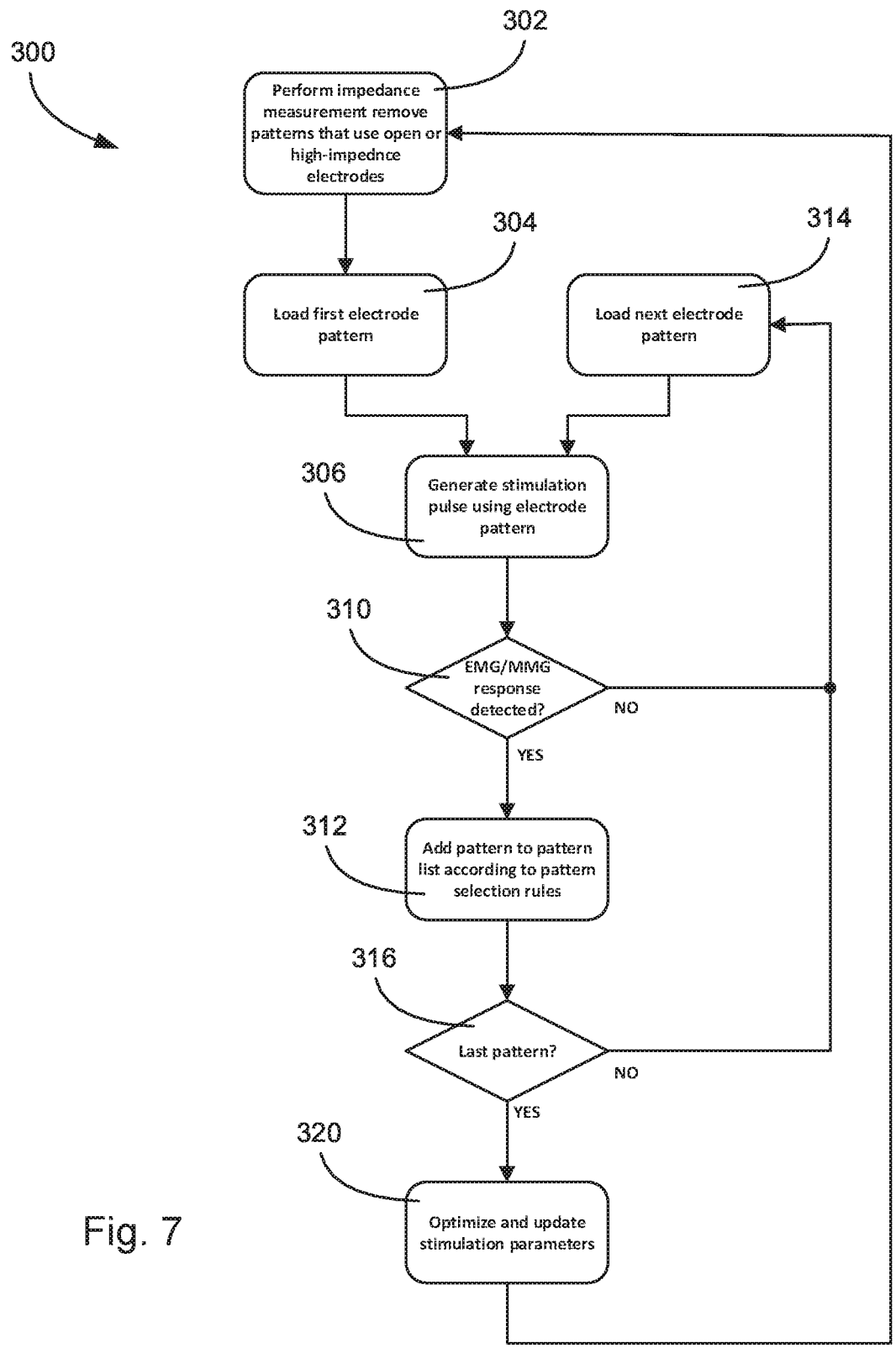

FIG. 7 is a flow chart illustrating an example nerve localization process implemented by the electronic medical device.

Figure 8:
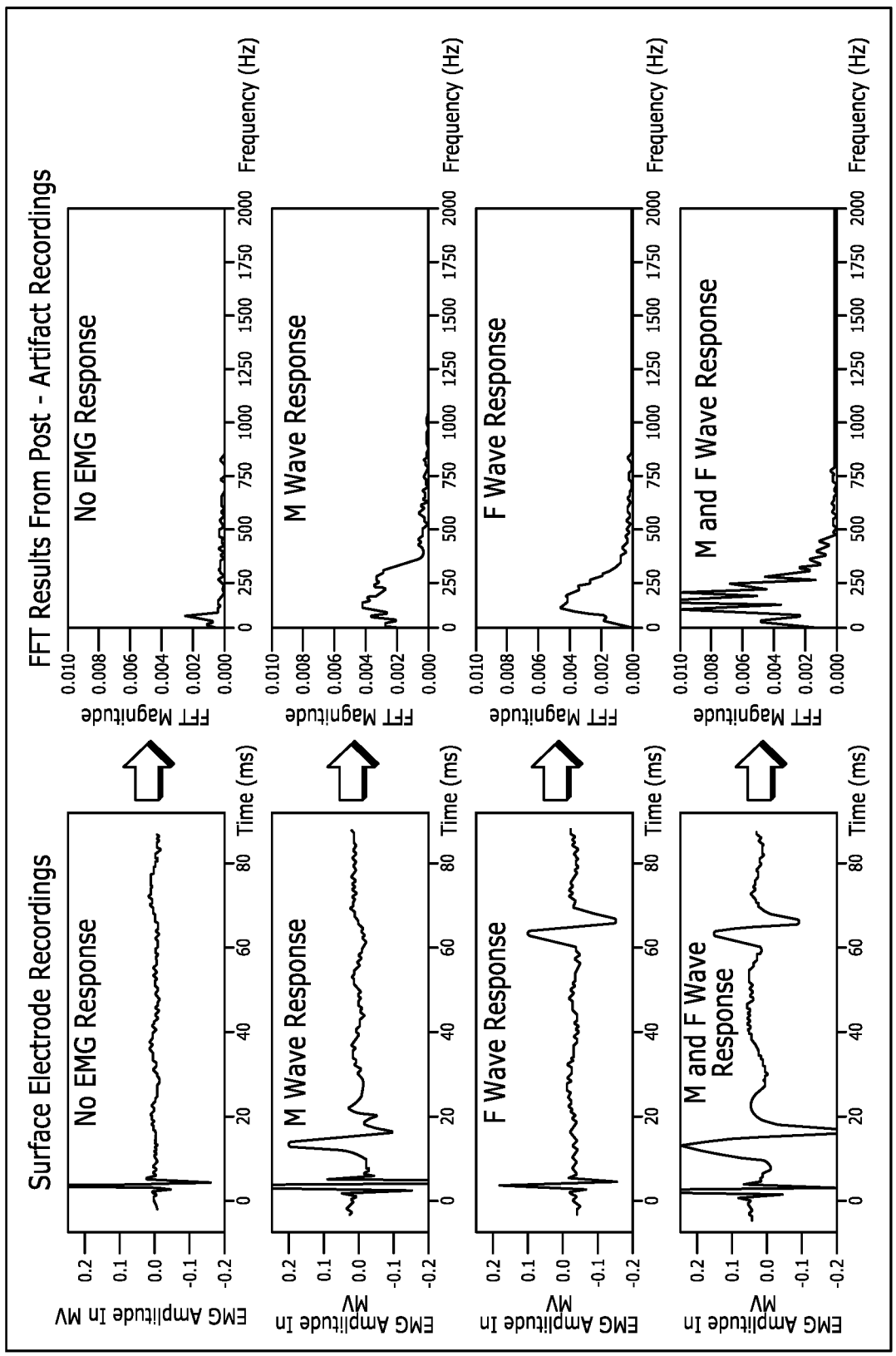

FIG. 8 is a series of charts illustrating examples of recorded EMG responses to electrical nerve stimulation.

Figure 9:
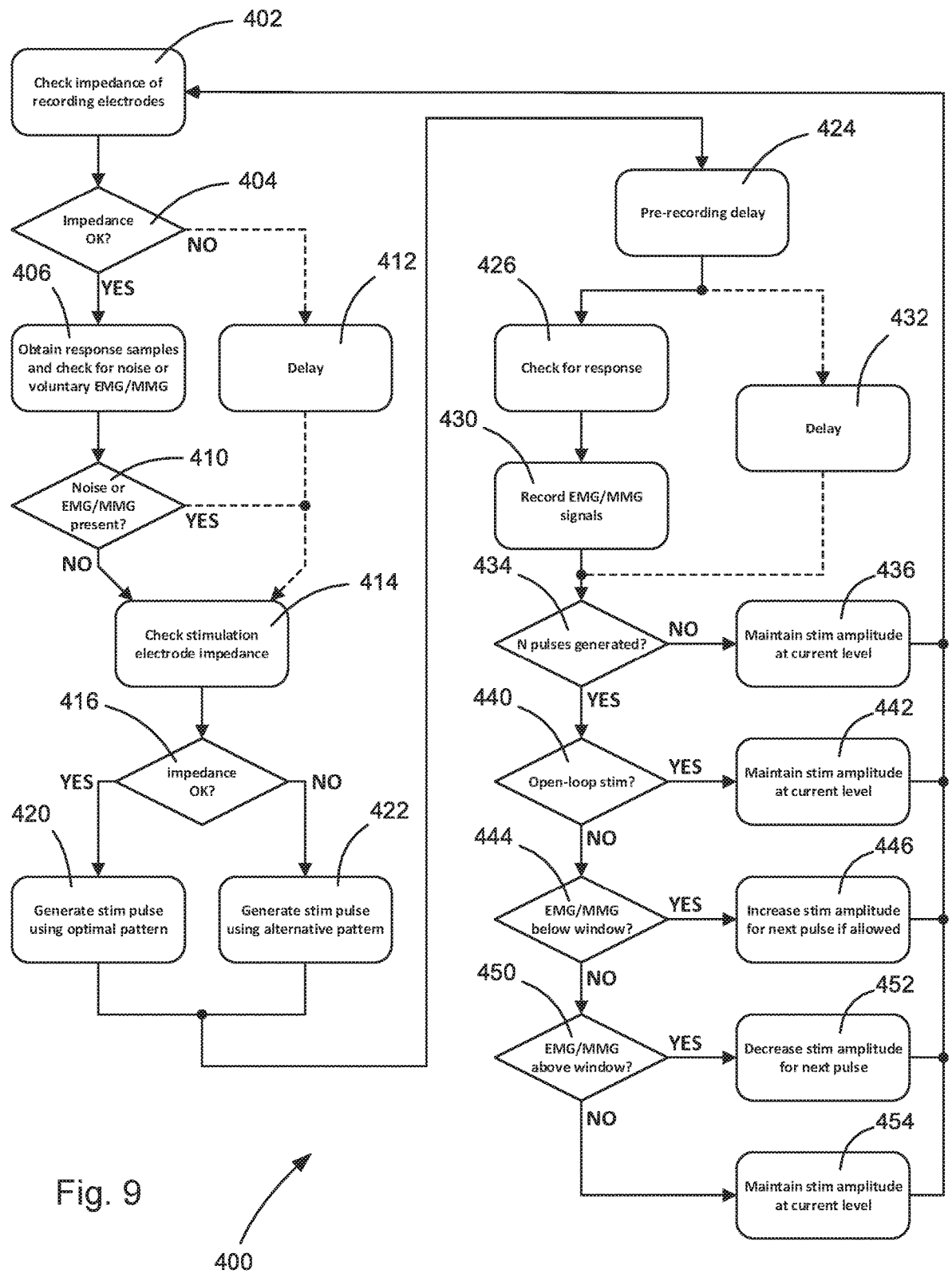

FIG. 9 is a flow chart illustrating an example open-loop and closed-loop electrical nerve stimulation processes implemented by the electronic medical device.

DESCRIPTION

An electronic medical device, a system including the medical device, and a method for using the medical device, is configured to apply transcutaneous electrical stimulation to peripheral nerves to treat various medical conditions.

For example, the system can be used to stimulate the tibial nerve (transcutaneous tibial nerve stimulation "TTNS") to treat medical conditions associated with pelvic floor dysfunction, e.g., over-active bladder (OAB). In a TTNS implementation, the electronic medical device applies electrical stimulation near the medial malleolus, which activates both sensory and motor fibers in the nerve. The activation of the sensory fibers of the tibial nerve helps to treat the urge-related symptoms of OAB. The activation of the motor fibers can, however, cause unwanted side effects, such as toe twitch or spasm.

As another example, the system can be used to apply electrical stimulation to the tibial nerve to treat sexual dysfunction. In this manner, it is believed that tibial nerve stimulation could be used to treat genital arousal aspects of female sexual interest/arousal disorder by improving pelvic blood flow.

As another example, the system can be applied to the wrist area to provide stimulation to the ulnar nerve and/or median nerve for pain management in carpal tunnel syndrome, hypertension management, and nerve conduction study/nerve injury diagnosis for median/ulnar nerve neuropathy, etc.

The system and/or the device employed by the system can have a variety of implementations. According to one implementation, the electronic medical device (i.e., the electrodes, control unit, wiring, etc.) can be fixed to a garment that is worn by the subject. The garment can be tight or snug-fitting so as to maintain sufficient contact between the subject's skin and can be configured to position the electrodes at locations specific to the peripheral nerves being stimulated. For example, to stimulate peripheral nerves in the area of the foot or ankle, such as the tibial nerve near the medial malleolus as described above, the garment can be in the form of a sock, ankle brace, strap, sleeve, or other like structure. For stimulating peripheral nerves on the leg, the garment can be a brace, strap, or sleeve sized appropriately for lower leg, knee, or upper leg positioning. For knee or ankle positioning, the garment can be configured, e.g., with openings, slots, or interconnected sections, to allow for bending with the joint while maintaining electrode positioning and contact.

Similarly, for stimulating peripheral nerves on the hand, the garment can be in the form of a glove, mitten, hand brace, or sleeve. For stimulating peripheral nerves on the arm, the garment can be a tight/snug fitting brace, strap, or sleeve (e.g., neoprene) that is sized appropriately for lower arm (forearm/wrist), elbow, or upper arm positioning. For wrist and/or elbow positioning, the sleeve can be configured, e.g., via openings, slots, or interconnected sections, to allow for bending with the joint while maintaining electrode positioning and contact.

In keeping with the above, it will be appreciated that the manner in which the electronic medical device can be secured or supported on the subject can vary. It will also be appreciated that the manner in which the electronic medical device is supported is not critical, as long as contact between the electrodes and the subject's skin is maintained, the positions of the electrode on the subject are maintained, and that the aforementioned are achieved in a manner that is comfortable to the subject.

Strap Implementation

FIGS. 1A-B illustrate a system comprising an example configuration of the electronic medical device 10 for providing transcutaneous electrical nerve stimulation, referred to herein as a neurostimulator, supported on a subject 12. The neurostimulator 10 of FIGS. 1A-B includes a garment in the form of a strap 20 that supports the neurostimulator and its components on the subject 12. In the example configuration of FIGS. 1A-B, the strap 20 connects the neurostimulator 10 to the subjects foot 14, with FIG. 1A illustrating a left foot implementation, and FIG. 1B illustrating a right foot implementation. In both instances, the strap 20 is wrapped figure-eight style, with one loop extending around the foot and one loop extending around the lower leg/ankle. Opposite end portions of the strap 20 can be interconnected, e.g., via a buckle or loop 22 and an end portion 24 of the strap that extends through the loop, is folded over, and connected to itself with a hook and loop fastener. The hook and loop fastener is shown in FIG. 2B and includes a hook portion 26 and loop portion 28.

The strap 20 implementation of the neurostimulator 10 is advantageous in that it is versatile and can be adapted to secure the neurostimulator to a wide variety of locations on the subject 12. The strap 20 can easily be wrapped around the foot 14 and/or ankle 16, as shown, and can also be wrapped around and secured to any location along the length of the subject's leg 18, either in a single loop or more than one loop, as the length of the strap permits. At the knee, the strap 20 can be wrapped, for example, in a figure-eight style in a manner similar to that illustrated in FIGS. 1A and 1B.

Referring to FIGS. 2A-B, the neurostimulator 10 includes a several of components that are secured or otherwise supported on the strap 20. The securement of these components can be achieved in a variety of manners, such as by adhesives, stitching, mechanical fastening, hook and loop fasteners, or a combination thereof.

The neurostimulator 10 includes stimulation electrodes 50 that are arranged in one or more arrays 52 and positioned on an inner surface 36 of the strap 20 at a widened end portion 30 of the strap. The number of stimulation electrodes 50, the area covered by the array 52, the electrode density (i.e., number of electrodes per unit area) in the array, and the distribution or pattern of electrodes within the array all can vary depending on the intended application of the neurostimulator 10. Additionally, the neurostimulator 10 can include more than one stimulation electrode array 52 again, depending on the application. In the example configuration of FIG. 2A, the stimulation electrode array 52 includes six stimulation electrodes 50 arranged in a generally elongated kidney-shaped manner. The number and arrangement of the stimulation electrodes 50, and the location/position of the electrode array 52 on the strap 20 are by way of example only and are by no means limiting.

In the example configuration of FIG. 2A, the stimulation electrodes 50 can be dry electrodes, in which case the neurostimulator 10 can include a removable/replaceable stimulation gel pad 54 shaped and sized to coincide with and cover the stimulation electrode array 52. In use, the gel pad 54 facilitates a strong, reliable electrical connection between the stimulation electrodes 50 and the subject's skin.

The neurostimulator 10 also includes dedicated recording electrodes 60 that are arranged in one or more arrays 62 and positioned on the inner surface 36 of the strap 20 spaced from the stimulation electrode array 52. The spacing between the stimulation electrodes 50 and the recording electrodes 60 can be important, as it can be necessary to provide adequate distance between the electrodes so that electrical stimulation signals can be separated or distinguished from responses (e.g., neurological, muscular, neuromuscular, etc.) to those electrical stimulation signals. This facilitates utilizing responses to stimulation sensed by the recording electrodes 60 as feedback in a closed-loop stimulation control scheme, which is described in detail below.

The number of recording electrodes 60, the area covered by the array 62, the electrode density (i.e., number of electrodes per unit area) in the array, and the distribution or pattern of electrodes within the array all can vary depending on the intended application of the neurostimulator 10. Additionally, the neurostimulator 10 can include more than one recording electrode array 62 again, depending on the application. In the example configuration of FIG. 2A, the recording electrode array 62 includes four electrodes 60 arranged linearly in two parallel rows of two electrodes. The number and arrangement of the recording electrodes 60, and the location/position of the electrode array 62 on the strap 20 are by way of example only and are by no means limiting.

In the example configuration of FIG. 2A, like the stimulation electrodes 50, the recording electrodes 60 can also be dry electrodes. Because of this, the neurostimulator 10 can also include a removable/replaceable gel pad 64 shaped and sized to coincide with and cover the recording electrode array 62. In use, the gel pad 54 facilitates a strong, reliable electrical connection between the recording electrodes 60 and the subject's skin.

Referring to FIG. 2B, the neurostimulator 10 also includes an electronic control unit 70 that is operative to control the application of transcutaneous electrical nerve stimulation via the stimulating electrodes 50 and to receive stimulation feedback gathered by the recording electrodes 60. The control unit 70 is located at the widened end 30 of the strap 20 on an outer surface 38, opposite the inner surface 36, of the strap 20. The buckle 22 can be a portion of the control unit 70 or can be connected to the control unit. In the example configuration of FIG. 2B, the control unit 70 has a generally elongated kidney-shaped configuration similar to that of the stimulating electrode array 52 and is positioned on the outer surface 38 generally opposite the stimulating electrode array. This is by no means necessary to the design of the neurostimulator 10, as the shape and location of the control unit 70 can vary.

In the example configuration of FIG. 2B, however, the shape and the positioning of the control unit 70 is convenient. The control unit 70 is detachably connected to the remainder of the neurostimulator 10 via a plug-in or snap-in connector 72 (see FIG. 2B), which receives a mating connector 74 (see FIG. 2D) on the control unit 70. FIG. 2B shows the control unit 70 connected to the neurostimulator 20 via the connector 72, and FIG. 2C shows the neurostimulator 20 with the control unit detached from the connector and removed. Configuring the control unit 70 to be detachable/removable allows the control unit to be utilized with other neurostimulator configurations and also allows the strap 20 and the components remaining on the strap (e.g., the electrodes, etc.) to be replaced when worn out, expired, or otherwise due for replacement.

Advantageously, the stimulating electrode array 52 can be part of an assembly in which the stimulating electrodes 50 can be mounted on a substrate or housing 56 constructed, for example of plastic. This substrate/housing 56 can itself be secured to the strap 20 (e.g., via adhesives, stitching, or mechanical fastening) to thereby secure the stimulation electrode array 52 to be strap. Forming the stimulating electrode array 52 in this manner facilitates a precise arrangement and spacing of the stimulation electrodes 50 and makes it easy to secure them to the strap 20.

The connector 72 can also be formed as a portion of the housing 56. The connector 72 can be configured to protrude from a side of the housing 56 opposite the stimulation electrodes 50. The connector 72 can, for example, extend through a hole in the strap 20 to position the connector on or extending from the outer surface 38. When the control unit 70 is connected to the connector 72, the strap 20 can be positioned between the control unit and the portion of the housing 56 supporting the stimulator electrode array 52.

The connector 72 can support a plurality of terminals for electrically connecting the control unit 70 to the stimulation electrodes 50 and the recording electrodes 60. Certain terminals in the connector 72 can be electrically connected to the stimulation electrodes 50 by wires or leads that are embedded within the plastic housing material (e.g., via insert molding). Embedding the leads in this manner helps maintain adequate spacing between the conductors, which avoids the potential for shorts in the circuitry.

Other terminals in the connector can be electrically connected to the recording electrodes 60 by wires or leads 66 that are partially embedded within the plastic housing material (e.g., via insert molding) and pass through the housing 56, extending to the feedback electrode arrays 62. Through this configuration, all of the necessary electrical connections to the stimulation and recording electrodes 50, 60 are made when the control unit 70 is installed on the connector 72.

The neurostimulator 10 also includes electrode backing 80 that facilitates safe storage and portability of the system. Fold lines 82, 84 shown in FIG. 2A indicate lines along which the neurostimulator 10/strap 20 can be folded to place the device in the stored condition. The steps involved in placing the neurostimulator 10 in the stored condition are illustrated in FIGS. 2C-2E.

As shown in FIG. 2C, the control unit 70 is detached from the housing 56. The control unit 70 is secured to the end portion 24 of the strap 20 by the hook and loop fastener 26, 28. Next, as shown in FIG. 2D, with the inner surface 36 facing up, the widened end portion 38 is folded over along the fold line 82, which places the stimulating electrode array 52 on a corresponding portion of the electrode backing 80. Next, as shown in FIG. 2E, the strap 20 is folded over along the fold line 84, which places the recording electrode array 62 on a corresponding portion of the electrode backing 80. This leaves the neurostimulator 10 in the stored condition of FIG. 2E.

To use the neurostimulator 10, the strap 20 is simply unfolded and the control unit 70 is connected to the housing 56 via their respective connectors 72, 74. The hook and loop fastener 26, 28 can be disconnected, the strap 20 wrapped around the appropriate anatomy of the subject, and the fastener re-connected to attach neurostimulator 10 to the subject. Conveniently, where the neurostimulator 10 is configured for stimulating the tibial nerve in the position illustrated in FIGS. 1A-B, the widened end 30 of the strap 20 can include a visual alignment cue 90, such as a hole in the strap, that becomes aligned with the medial malleolus of the ankle when the stimulating electrodes are properly positioned.

Brace Implementation

FIGS. 3A-B illustrate a system comprising another example configuration of an electronic medical device 110 for providing transcutaneous electrical nerve stimulation, referred to herein as a neurostimulator, supported on a subject 112. The neurostimulator 110 of FIGS. 3A-1B includes a garment in the form of a brace 120 that supports the neurostimulator and its components on the subject 112. In the example configuration of FIGS. 3A-B, the brace 120 connects the neurostimulator 110 to the subject's foot 114, with FIG. 3A illustrating a left foot implementation, and FIG. 3B illustrating a right foot implementation. In both instances, the brace 120 has an upper portion 130 wrapped around the lower leg/ankle and a lower portion 150 portion wrapped around the foot/ankle. Each of these portions are secured to the subject via a connection such as a hook and loop fastener.

The brace 120 implementation of the neurostimulator 10 is advantageous in that it is versatile in its ability to position the stimulating electrodes and recording electrodes at different locations on the subject. For example, stimulating electrodes can be positioned on the upper portion 130 of the brace 120 wrapped around the ankle, and recording electrodes can be positioned on the lower portion 150 of the brace wrapped around the foot. This can be especially advantageous for closed-loop neurostimulation of the tibial nerve. In this implementation, stimulating electrodes on the upper portion 130 can be located between the medial malleolus and the Achilles tendon to provide electrical stimulation to the tibial nerve. Recording electrodes on the lower portion 150 can be located on the bottom of the subject's foot, near the flexor muscles (abductor hallucis and the flexor hallucis brevis) for the big toe and can record the EMG signals that result from recruitment of the tibial nerve's motor fibers.

As another advantage, the brace 120 is configured for placement at or about a subject's joint and provides for movement of that joint. While the brace 120 is illustrated as being applied at the subject's ankle joint, it will be appreciated that the brace 120 can also be applied at the knee joint or elbow joint. Additionally, positioning the brace 120 at a joint is not critical, as it can be seen that the brace can be applied at any location along the subject's arms or legs, size permitting.

The construction of the neurostimulator 110 is illustrated in FIGS. 4A-D. For the example configuration of FIGS. 4A-D the upper portion 130 and lower portion 150 of the strap 120 are separate components that are interconnected by adjustment bands 122. The adjustment bands 122 can allow for adjusting the spacing between the upper and lower portions 130, 150, e.g., via a buckle or hook and loop fastener, or the bands can be of a fixed size amongst a range of sizes, e.g., x-small, small, medium, large, x-large, etc. The respective sizes of the upper and lower portions 130, 150 can be similarly sized. In fact, the upper portion 130 can itself be composed of first and second portions 132, 134 connected by a band 136 that allows for adjusting the spacing between the upper and lower portions 130, 150, e.g., via a buckle or hook and loop fastener.

The upper portion 130 of the brace 120 includes a hook and loop fastener composed of a hook portion 140 and a loop portion 142, which are positioned opposite each other along an upper extent of the upper portion. The upper portion 130 also includes opposite tab portions 144 to which the adjustment tabs 122 (see, FIGS. 4C-D) are connected, e.g., via stitching. Similarly, the lower portion 130 of the brace includes a hook and loop fastener composed of a hook portion 152 and a loop portion 154, which are positioned opposite each other along a lower extent of the lower portion. The lower portion 150 also includes opposite tab portions 156 to which the adjustment tabs 122 (see, FIGS. 4C-D) are connected, e.g., via stitching.

The neurostimulator 110 includes a several of components that are secured or otherwise supported on the brace 120. The securement of these components can be achieved in a variety of manners, such as by adhesives, stitching, mechanical fastening, hook and loop fasteners, or a combination thereof. FIGS. 4A and 4B illustrate the neurostimulator 110 in a partially assembled condition, with the electronic components of the neurostimulator mounted on the brace 120 prior to the first and second portions 132, 134 being interconnected by the adjustment bands 122. This construction is advantageous because it allows the electronic components of the neurostimulator 110 to be assembled onto brace 120 while the upper and lower portions 130, 150 lie flat. The lying flat illustration of FIGS. 4A-B is for purposes of simplicity as it allows the upper and lower portions 130, 150 to be illustrated lying flat. FIG. 4A illustrates an inner surface 124 of the brace 120. FIG. 4B illustrates an outer surface 126 of the brace 120.

The neurostimulator 110 includes stimulation electrodes 170 that are arranged in one or more arrays 172 and positioned on the inner surface 124 of the upper portion 130 of the brace 120. In the example configuration illustrated in FIG. 4A, the stimulation electrode arrays 172 are positioned on opposite sides of the adjustment band 136 connecting the first and second portions 132, 134 of the upper portion 130. This arrangement can, for example, allow the brace 130 implementation of the neurostimulator 110 to be ambidextrous.

The number of stimulation electrodes 170, the area covered by the stimulation electrode arrays 172, the electrode density (i.e., number of electrodes per unit area) in the arrays, and the distribution or pattern of electrodes within the array all can vary depending on the intended application of the neurostimulator 110. In the example configuration of FIG. 4A, each stimulation electrode array 172 includes six stimulation electrodes 170 arranged in a generally rectangular manner in two rows of three electrodes. The number and arrangement of the stimulation electrodes 170, and the location/position of the electrode array 172 on the brace 120 are by way of example only and are by no means limiting.

In the example configuration of FIG. 4A, the stimulation electrodes 170 can be dry electrodes, in which case the neurostimulator 110 can include one or more removable/replaceable stimulation gel pads 174 shaped and sized to coincide with and cover the stimulation electrode array 172. In use, the gel pads 174 facilitate a strong, reliable electrical connection between the stimulation electrodes 170 and the subject's skin.

The neurostimulator 110 also includes recording electrodes 180 that are arranged in one or more arrays 182 and positioned on the inner surface 124 of the lower portion 150 of the brace 120 at a location spaced from the stimulation electrode arrays 172. The spacing between the stimulation electrodes 170 and the recording electrodes 180 can be important, as it can be necessary to provide adequate distance between the electrodes so that electrical stimulation signals can be separated or distinguished from responses (e.g., neurological, muscular, neuromuscular, etc.) to those electrical stimulation signals. This facilitates utilizing responses to stimulation sensed by the recording electrodes 180 as feedback in a closed-loop stimulation control scheme which, again, is described in detail below.

The number of recording electrodes 180, the area covered by the array 182, the electrode density (i.e., number of electrodes per unit area) in the array, and the distribution or pattern of electrodes within the array all can vary depending on the intended application of the neurostimulator 110. In the example configuration of FIG. 4A, there are two recording electrode arrays 182, each of which includes two recording electrodes 180 arranged linearly. The number and arrangement of the recording electrodes 180, and the location/position of the electrode arrays 182 on the brace 120 are by way of example only and are by no means limiting.

In another implementation, the neurostimulator 110 can be configured to include MMG sensors (e.g., accelerometers) for sensing muscle movement as opposed to electrical activity. The optional MMG sensors are illustrated in dashed lines at 186 in FIG. 4A. In this implementation, the MMG sensors 186 can be implemented in addition to or in place of, the EMG electrodes 180. Implementing the MMG 186 sensors along with the EMG sensors 180 can prove beneficial in that the combination can provide additional functionality. For example, the MMG sensor 186 can be used to confirm the validity of an EMG measured feedback response. Additionally, the MMG sensors 186 (or any other accelerometer for that matter) can be used to verify that the subject in a resting, i.e., not moving, condition prior to initiating a therapy session.

In the example configuration of FIG. 4A, like the stimulation electrodes 170, the recording electrodes 180 can also be dry electrodes. Because of this, the neurostimulator 110 can also include a removable/replaceable recording gel pad 184 shaped and sized to coincide with and cover the recording electrode arrays 182. In use, the gel pad 184 facilitates a strong, reliable electrical connection between the recording electrodes 180 and the subject's skin.

Referring to FIG. 4B, the neurostimulator 110 also includes an electronic control unit 200 that is operative to control the application of transcutaneous electrical nerve stimulation via the stimulating electrodes 170 and to receive stimulation feedback gathered by the recording electrodes 180. The control unit 200 is located on the outer surface 126 of the upper portion 130 adjacent the adjustment band 136 and opposite one of the stimulating electrode arrays 172 on the inner surface 124 of the upper portion. In the example configuration of FIG. 4B, the control unit 200 has a generally elongated racetrack-shaped configuration similar, to that of the stimulating electrode arrays 172, although narrower. This is by no means necessary to the design of the neurostimulator 110, as the shape and location of the control unit 200 can vary.

In the example configuration of FIG. 4B, however, the shape and the positioning of the control unit 200 is convenient. The control unit 200 can be detachably connected to the remainder of the neurostimulator 110 via a plug-in or snap-in connector, such as by a connector (not shown) that is similar or identical to the connector associated with the control unit of the example configuration of FIGS. 2A-D. Configuring the control unit 200 to be detachable/removable allows the control unit to be utilized with other neurostimulator configurations and also allows the brace 120 and the components remaining on the brace (e.g., the electrodes, etc.) to be replaced when worn out, expired, or otherwise due for replacement.

Advantageously, each stimulating electrode array 172 can be part of an assembly in which the stimulating electrodes 170 can be mounted on a substrate or housing 176 constructed, for example of plastic. This substrate/housing 176 can itself be secured to the brace 120 (e.g., via adhesives, stitching, or mechanical fastening) to thereby secure the stimulation electrode array 172 to be brace. Forming the stimulating electrode array 172 in this manner facilitates a precise arrangement and spacing of the stimulation electrodes 170 and makes it easy to secure them to the brace 120.

In a manner similar or identical to that of the example configuration of FIGS. 2A-D, the connector of each stimulating electrode array 172 can also be formed as a portion of the housing 176. The connector can be configured to protrude from a side of the housing 176 opposite the stimulation electrodes 170. The connector can, for example, extend through a hole in the brace 120 to position the connector on or extending from the outer surface 126. When the control unit 200 is connected to the connector, the brace 120 can be positioned between the control unit and the portion of the housing 176 supporting the stimulator electrode array 172.

Again, in a manner similar or identical to that of the example configuration of FIGS. 2A-D, the connector can support a plurality of terminals for electrically connecting the control unit 200 to the stimulation electrodes 170 and the recording electrodes 180. Certain terminals in the connector can be electrically connected to the stimulation electrodes 170 by wires or leads that are embedded within the plastic housing material (e.g., via insert molding). Embedding the leads in this manner helps maintain adequate spacing between the conductors, which avoids the potential for shorts in the circuitry.

Other terminals in the connector can be electrically connected to the recording electrodes 180 by wires or leads 184 that are partially embedded within the plastic housing material (e.g., via insert molding) and pass through the housing 176, extending to the recording electrode arrays 182. Through this configuration, all of the necessary electrical connections to the stimulation and recording electrodes 170, 180 are made when the control unit 200 is installed on the neurostimulator 110.

Referring to FIGS. 4C-D, the neurostimulator 110 is assembled by connecting the first and second portions 132, 134 of the upper portion 130 with the adjustment band 136. The upper and lower portions 130, 150 are interconnected by two adjustment bands 122 that interconnect their respective tab portions 144, 156. This completes the assembly of the neurostimulator 110, placing it in a condition to be worn by the subject in the manner illustrated in FIGS. 3A-B.

To use the neurostimulator 110, the brace 120 is simply unfolded and the control unit 200 is connected to the housing 176 via the connectors. The hook and loop fasteners 140, 142 and 152, 154 are disconnected, the brace 120 wrapped around the appropriate anatomy of the subject. In FIGS. 3A-B, the upper portion 130 is wrapped around the lower leg/ankle 112 of the subject, and the lower portion 150 is wrapped around the foot 114 of the subject. The hook and loop fasteners 140, 142 and 152, 154 are re-connected to attach neurostimulator 110 to the subject. Conveniently, where the neurostimulator 110 is configured for stimulating the tibial nerve in the position illustrated in FIGS. 3A-B, the upper portion 130 of the brace 120 can include visual alignment cues 210, such as holes in the brace, that become aligned with the medial malleolus of the ankle when the stimulating electrodes 170 are properly positioned.

Control Unit Configuration

The control units 70, 200 of the example configurations of the neurostimulator 10, 110 of FIGS. 1A-4D can have a variety of configurations. An example configuration for the control units 70, 110 is shown in FIG. 5. Referring to FIG. 5, the control unit 70, 200 includes a microcontroller 220 powered by a primary or rechargeable battery 222 via a battery protection and charging circuit 224. The circuit 224 offers battery protection typical for a medical device, such as over-current and over-voltage protection, under-voltage protection, and a charging controller. An external cable or charging cradle 226 charges the battery 222 via the circuit 224. Alternatively, the battery 222 can be charged wirelessly, e.g., via a wireless charging cradle. A pushbutton 228 cycles on/off power to the control unit 70, 200.

The battery protection and charging circuit 224 also marshals power to a high voltage power supply circuit 230, a digital power supply circuit 232, and an analog power supply circuit 234. The high-voltage power supply circuit 230 is used to provide a stimulation compliance voltage to the output stage's current sources and sinks. Since this device is a transcutaneous stimulator, it can require a compliance voltage in the range of about 40-200 V or more in order to provide the necessary current to stimulate the tibial nerve. For this embodiment, a compliance voltage of 120 volts is used for the compliance voltage.

A radio controller 240, such as a Bluetooth® or Zigbee® radio controller, provides a communication input to the microcontroller 220 for functions such as programming the control unit 70, 200, uploading/downloading data, and monitoring/controlling the neurostimulator 10, 110 during use. The radio controller 240 could, for example, pair the microcontroller to an enabled device, such as a smartphone, tablet, or computer, executing software that enables the user to monitor or otherwise control the operation of the neurostimulator 10, 110. The microcontroller 220 controls the operation of indicators 242, such as LEDs, that indicate the state or condition of the control unit 70, 210. The microcontroller 220 can control an accelerometer 244, which can provide input to determine whether the neurostimulator 10, 110, and thus the subject, is moving or at rest.

The microcontroller 220 is responsible for controlling the stimulation output, measuring the electrode impedance, and processing the EMG response. The microcontroller 220 runs software for performing these functions, including decision-making algorithms to allow the device to provide the desired therapy. The microcontroller 220 controls the operation of an amplitude control circuit 250, a timing control circuit 252, and a digital-to-analog converter (DAC) 254. By "circuit," it is meant that these functions can be implemented in any desired manner, e.g., through discrete components, integrated circuits, or a combination thereof. The amplitude control circuit 250, timing control circuit 252, and DAC 254 drive a stimulator output stage 260, which provides stimulator output signals (e.g., pulse-width-modulated "PWM" output signals) to one or more analog output switches 262. The output switch(es) 262 are operatively connected to a port 280 comprising a plurality of terminals (E1-E8 in FIG. 5) that facilitates connecting the control unit 70, 200 to the stimulator and recording electrodes, for example, via the leads 66, 184 (see, FIGS. 2A and 4B, respectively). Through this connection via the leads 66, 184, the stimulator output stage 260 can be operatively connected to the stimulator electrodes 50, 170.

The microcontroller 220 receives electrode impedance values via an impedance measurement circuit 264 that is operatively connected to the stimulator output stage 260. The microcontroller 220 also receives electrode feedback values (e.g., F-wave and M-wave values) via an analog front end 270 that is operatively connected to one or more analog input switches 272. The input switch(es) 272 are also operatively connected to the terminals/port 280 and can thereby receive feedback from the recording electrodes 60, 180 that facilitates connecting the control unit 70, 200 to the stimulator and recording electrodes, for example, via the leads 66 (see, FIG. 2A) or 184 (see, FIG. 4B).

The impedance measurement circuit 264 allows for measuring the impedance of the electrodes. It is important to measure the impedance often, in case one or more of the electrodes begins to lift from the skin. There are two potential hazards related to electrode lifting that should be mitigated. First, if an electrode is partially lifted from the skin, the surface area of the electrode that is in contact with the skin is reduced and the current density of the stimulation current is increased, which can be unsafe. Second, if an active electrode is completely lifted from the skin, a brief but large amount of energy can be delivered to the tissue when the electrode makes contact with the skin, which can result in pain.

Electrode impedances measured via the impedance measurement circuit 264 can also be used as an additional input for a closed-loop stimulation optimization algorithm.

The stimulator output stage 260 provides the current to the stimulating electrodes via the output switch 262. Each channel of the output stage includes a current source and current sink, which allows each channel to provide either a positive or negative current to the tissue through the corresponding stimulation electrode(s) 50, 170. In this configuration, each current source and sink can have independently programmable amplitude control 250 and timing control 252, which provides the capability to "steer" the current applied via the stimulation electrodes 50, 170, as described below. The programmable range can vary depending on the application, and is selected to be capable of achieving the desired nerve recruitment. In an example configuration, the current sources can have a programmable range from zero to +20 milliamperes (mA), and the current sinks can have a programmable range from zero to −20 mA.

As shown in FIG. 5, the analog output switches 262 and input switches 272 can both be operatively connected to each of the terminals E1-E8. Through operation of the switches 262, 272 as commanded by the microcontroller 220, the identity or role of the terminals, i.e., output terminal or input/feedback terminal, can be actively identified. This allows the microcontroller 220 to selectively identify, activate, and deactivate electrodes in a desired pattern, order, combination, etc., according to the particular therapy regimen being applied. This also allows the therapy to be tailored, for example, in response to signals received from the recording electrodes.

Control Overview

According to one example implementation, the neurostimulator 10, 100 described above can control the application of stimulation therapy according to two general phases: nerve localization and stimulation delivery. These two phases work synergistically to provide the functionality set forth in the following paragraphs.

During the nerve localization phase, the target peripheral nerve structure, e.g., the tibial nerve, is localized when the neurostimulator 10, 100 is donned and activated. In the nerve localization phase, the neurostimulator 10, 100 implements a process in which the following functions are performed:

Ramping up stimulation energy across various electrode patterns.
Monitoring EMG response after each stimulation pulse.
Determining the electrode pattern and stimulation parameters that optimally activate the target peripheral nerve.

During the stimulation delivery phase, electrical stimulation is delivered to the target peripheral nerve structure using the electrode pattern(s) and stimulation parameters determined during the nerve localization phase. In the stimulation delivery phase, the neurostimulator 10, 100 implements a process in which the following functions are performed:

Deliver stimulation pulses to the target peripheral nerve.
Continuously optimize the delivery of stimulation pulses, which includes:
Monitoring EMG response after each stimulation pulse.
Monitoring electrode impedance.
Adjusting either the electrode pattern (current-steering) or stimulation energy to optimize recruitment of the tibial nerve.
Automatically stopping stimulation at the end of the therapy session.

The nerve localization and stimulation delivery phases are described in more detail in the following sections.

Nerve Localization

In practice, the control unit 110 can be programmed with a set of electrode patterns that identify which stimulation electrode 50, 170 in an electrode array 52, 172 are active, and also the polarity or type, i.e., anode (+) or cathode (−) assigned to the electrode. FIG. 6 illustrates an example configuration for an electrode array 52, 172 and a chart illustrating an example set of electrode patterns. In the example illustrated in FIG. 6, the electrode array 52, 172 has eight electrodes 50, 170, identified at E1-E8, and the chart identifies ten different electrode patterns (patterns 1-10) for the electrode array. For each electrode pattern, each electrode is identified as being a cathode (C), anode (A), or inactive (blank). Thus, for example, in pattern 3, electrodes E1 and E2 are cathodes, electrodes E5 and E6 are anodes, and electrodes E3, E4, E7, and E8 are inactive. While there are a large number of patterns that are possible with an eight-electrode array, the patterns can effectively be narrowed down to a shorter list, such as the illustrated 10 patterns or more, depending on the nerve under recruitment.

The neurostimulator 10, 110 can be configured to perform a nerve localization routine to determine which of the electrode patterns should be utilized on a subject. In the example configuration of FIG. 6, the electrode array 52, 172 can be specifically designed, i.e., shaped and electrodes positioned, to stimulate the tibial nerve in the region between the medial malleolus and the Achilles tendon. The electrode array 52, 172 can be configured to perform stimulation on this or other regions where peripheral nerve stimulation is desired.

In the example configuration of FIG. 6, the electrode array 52, 172 is curved to allow the medial malleolus to be used as a placement guide. Also, the array can be symmetrical so that it can be placed on either ankle. The electrode arrangement within the array must be configured to capture the tibial nerve, meaning that the nerve must pass below or between at least one pair of electrodes. If the tibial nerve passes outside the extents of the array, activation of the tibial nerve requires much higher stimulation energies, or it may not be possible to activate the tibial nerve at all.

The purpose of using an array for stimulation (as opposed to a single pair of electrodes) is to create an optimized stimulation field for recruiting the target (e.g., tibial) nerve. If the stimulation field is too small, the nerve will not be recruited and therapy will not be delivered. If the stimulation field is too large, too many motor neurons will be recruited resulting in undesired effects, such as pain, twitching, or muscle spasm. In order to optimize the stimulation field, the ability to steer current using multiple electrodes if preferred. For example, electrode pattern 8 assigns electrodes E3 and E4 as anodes and electrodes E7 and E8 as cathodes. Viewing the arrangement of these electrodes 50, 170 on the array 52, 172, it can be seen that the use of this electrode pattern could be effective on a nerve path that passes directly adjacent or between these electrode pairs.

By selecting the appropriate stimulation electrodes 50, 170 from the stimulation electrode arrays 52, 172, and varying the amplitude and polarity of the current applied via the selected electrodes, the electric field applied to the subject can be shaped so that the current is steered to the target nerves. By shaping the field, the neurostimulator 10, 100 can automatically adjust to day-to-day donning and placement variability for a given subject. Current steering also allows the neurostimulator 10, 100 to work across a subject population with wide anatomical variation, for example providing a shallow field for subjects with nerves that are superficial to the skin, or a penetrating field for subjects with nerves that are deep. In the illustrated example configurations, the stimulation electrode arrays 52, 152 include six electrodes. Any number of stimulation electrodes greater than one can be used. In general, the "field steering" capability of the neurostimulator 10, 100 increases with the number of stimulating electrodes 50, 170 that are included.

Because there will be session-to-session variability in the location of the stimulating electrode array 52, 172 due to the don/doff process, as well as variability in skin/tissue impedance, providing open-loop stimulation applying rigid pre-programmed stimulation parameters could be disadvantageous, often providing too little or too much stimulation energy to recruit the nerve. Advantageously, the nerve localization algorithm is executed at the beginning of each therapy session to determine which of the preprogrammed electrode patterns will be most effective.

FIG. 7 illustrates a flowchart showing the method or process 300 implemented by the nerve localization algorithm. The steps in the process 300 are not meant to be exclusive, i.e., other steps can be included. Nor is the process 300 intended to be strictly followed in terms of the order shown in FIG. 7 or described herein. The process 300 illustrates steps, perhaps a minimum, necessary to localize the peripheral nerve that is to be stimulated.

It should be noted here that, the process 300 is a closed-loop algorithm that utilizes feedback recorded via the recording electrodes 60, 180 to make determinations and/or adjust settings. As such, the process 300 relies on utilization of the feedback to determine which of the electrode patterns effectively achieves nerve recruitment. Specifically, the process 300 relies on feedback from the recording electrodes 60, 180 to provide indication of EMG response feedback. Alternatively, the process 300 can rely on accelerometers to provide MMG response feedback.

Referring to FIG. 7, the process 300 begins at step 302, where an impedance measurement is performed in order to determine which, if any, of the electrodes E1-E8 have open or prohibitively high impedance. This step 302 can be considered an integrity check for the electrodes 50, 170 in the array 52, 172 to determine if any of the electrodes in the array are not sufficiently contacted with the skin. If any of the electrodes in the array are determined to be performing in a substandard manner, indicated by displaying an open (infinitely high) or sufficiently high impedance, those electrodes and the electrode patterns that utilize those electrodes can be eliminated from use.

For example, in the example of FIG. 6, it can be seen from row 2 that electrode E6 has high impedance. In this instance, electrode patterns 3, 6, 7, and 9 are eliminated form use in the current therapy session. Alternatively, the algorithm could instruct the control unit to provide some indication to the user, such as an alarm or display, to re-position or adjust the electrodes to see if contact can be improved.

To avoid interfering with stimulation and EMG measurement, the integrity check at step 302 can be completed in a short amount of time, such as 25 milliseconds or less. Also, the impedance measurement can be conducted so as to cause little or no sensation in the subject's skin. Therefore, the excitation current for performing the integrity check should be low-amplitude, such as 1 mA or less. For the integrity check 302, the impedance value at each electrode is not critical. Instead, determining whether the impedance is below a certain threshold is adequate.

Additionally, conditions other than high or low impedance can be determined in this integrity check. For example, indicators such as dry/wet contact checks, whole/brittle/fractured contact checks, contact surface area checks, and contact reflectance checks can be made during the connectivity evaluation. Sensors, such as don/doff, stretch, strain, bending or contact sensors (via electrical, optical or mechanical means) can also be used for conducting the connectivity evaluation. These sensors could also be incorporated into a buckle, clasp, snap, hook/eye or zipper feature.

Once the integrity check is performed, the process 300 proceeds to step 304 where the first electrode pattern (that hasn't been eliminated by the integrity check) is loaded. The process 300 then proceeds to step 306 where the neurostimulator 10, 110 generates stimulation pulse(s) using the electrode pattern loaded in step 304. The process 300 proceeds next to step 310, where a determination is made as to whether the stimulation pulses generated at step 306 elicited an EMG response, i.e., feedback measured via the recording electrodes. Step 310 can additionally or alternatively determine whether there is a MMG response where the feedback devices include accelerometer(s).

If, at step 310, EMG (or MMG) is not detected, the process 300 reverts to step 314, where a new electrode pattern is loaded. The process 300 then proceeds to step 306, as described above. If, at step 310, EMG (or MMG) is detected, the process 300 proceeds to step 312, where the electrode pattern is added according to pattern selection rules. The process 300 then proceeds to step 316, where a determination is made as to whether the current electrode pattern is the last electrode pattern in the list.

The pattern selection rules at step 312 for adding an electrode pattern can be defined to prioritize electrode patterns identified as being the best suited to recruit the target nerves. These pattern selection rules may be implemented as follows:

If one pattern is significantly better than the others (e.g., as determined from the EMG data, see below), that pattern should be used as the primary pattern moving forward.

If two or three patterns are roughly equivalent, any one of the patterns can be used as the primary pattern. Moving forward, this pattern can be switched to other ones if the nerve recruitment displayed by the current primary pattern begins to diminish.

If the nerve recruitment for a particular pattern begins to diminish and increasing the stimulation parameters does not fix the problem, similar patterns can be re-introduced to the algorithm.

If, at step 316, it is determined that the current electrode pattern is not the last pattern in the list, the process 300 reverts to step 314, where a new electrode pattern is loaded. The process 300 then proceeds to step 306, as described above. If, at step 316, it is determined that the current electrode pattern is the last pattern in the list, this indicates that the pattern list is complete. The process 300 proceeds to step 320 where the stimulation parameters for the electrode patterns in the pattern list are optimized. At step 320, the stimulation parameters (e.g., frequency, amplitude, pattern, duration, etc.) are updated to optimize the nerve recruitment for each pattern. The process 300 then reverts back to the initial step at 302 and proceeds as described above. If the recruitment for a given electrode pattern improves, the stimulation parameters are kept. If not, they revert back to previous values. This process repeats itself until the pattern list is filled with electrode patterns optimized for nerve recruitment.

From the above, it will be appreciated that the nerve localization process 300 determines which of the electrode patterns to utilize and which to discard for any given stimulation therapy session, and then optimizes the stimulation parameters for the utilized patterns. The execution of this process 300 is fast. During execution, the neurostimulator 10, 110 applies stimulation therapy pulses via the stimulating electrodes 50, 170 and monitors for EMG responses via the recording electrodes 60, 180 after each pulse.

The analog front end circuit 270 can replace traditional EMG measurement circuitry such as a filter, amplifier, rectifier, and/or integrator. The control unit 110 utilizes the analog front-end circuit 270 to sample the recording electrodes at a predetermined sample rate, such as 1,000-8,000 samples per second. The EMG sampling window will begin after the stimulation pulse is finished, and the window will last for a predetermined brief period, such as 8-90 milliseconds. The resulting EMG data, comprised of M-wave or F-wave or both, will be analyzed using a Fast Fourier Transform (FFT) technique that clearly shows if EMG is present.

To execute the process 300 of FIG. 7, the neurostimulator 10, 110 monitors for electromyogram (EMG) signals via the recording electrodes 60, 180 in response to stimulation applied via the stimulation electrodes 50, 170. FIG. 8 illustrates examples of the EMG responses that can be recorded, which include: No EMG Response, F-wave Response, M-wave Response, and M and F-wave Response. In the example where no EMG response is recorded, the stimulation pulse artifact can be seen on the left, with no response following. In the example where an M-wave response is recorded, the stimulation pulse artifact can be seen on the left, followed by the M-wave at about 6 to 10 ms post-stimulation. In the example where an F-wave response is recorded, the stimulation pulse artifact can be seen on the left, followed by the F-wave responses at about 50 to 55 ms post-stimulation. In the example where both an M-wave and F-wave responses are recorded, the stimulation pulse artifact can be seen on the left, followed by the M-wave and F-wave at 6 to 10 ms and about 50 to 55 ms post-stimulation, respectively. These response times could change slightly, depending on a variety of factors, such as the hydration and/or salinity of the subject tissue, the arrangement and spacing of the electrodes, and the characteristics of the stimulation signals.

For each of the four recorded response scenarios, FIG. 8 also illustrates a corresponding Fast Fourier Transform (FFT) results for the raw post-artifact signal. The FFT results are calculated by the microcontroller 220 and are used in the process 300 to determine whether an EMG response is present (see, step 310 in FIG. 7).

Stimulation Delivery

The neurostimulator 10, 110 can apply stimulation therapy using an open-loop control scheme, a closed-loop control scheme, or a combination of open-loop and closed-loop control schemes, depending on the control algorithm programmed into the microcontroller 220. For open-loop control, the control units 70, 200 can apply electrical stimulation via the stimulation electrodes 50, 170 according to settings (frequency, amplitude, pattern, duration, etc.) without regard to any feedback measured via the recording electrodes 60, 180. This is not to say that feedback is not measured, just that, in an open-loop control scheme, the feedback is not used to inform or control the algorithm executed by the microcontroller 220 to control the application of stimulation therapy. In a closed-loop control scheme, the neurostimulator 10, 110 implements a control algorithm in which feedback from the recording electrodes 60, 180 informs and helps control the application of stimulation therapy.

FIG. 9 illustrates by way of example a process 400 by which the neurostimulator 10, 110 controls the application of electrical nerve stimulation using the electrode pattern(s) identified by the nerve localization process 300 of FIG. 7. The stimulation control process 400 can employ both open-loop and closed-loop control, with closed-loop steps or portions of the process being illustrated in solid lines and open-loop steps or portions being illustrated in dashed lines. Ideally, the process 400 will proceed with closed-loop control, as it is able to utilize feedback to optimize the application of stimulation therapy.

The process 400 begins at step 402, where the impedances of the recording electrodes 60, 180 are checked. If, at step 404, it is determined that the recording electrode impedances are too high (e.g., resulting in unavailable or unreliable feedback), the process 400 then shifts to open-loop mode (see dashed lines) and proceeds to step 412, where a delay is implemented. The purpose of delay 412 is to assist in maintaining a constant stimulation period, meaning that the duration of delay 412 should be equal to the duration of closed-loop step 406. After completing delay 412, the process 400 proceeds to step 414, where the stimulation electrode impedances are checked.

At step 404, if the impedances of the recording electrodes are acceptable, the process 400 remains in closed-loop mode and proceeds to step 406, where samples are obtained via the recording electrodes to check for significant noise or voluntary EMG responses. At step 410, if noise or EMG are present, the feedback is considered unreliable and the process 400 shifts to open-loop mode and proceeds to step 414. At step 410, if significant noise or voluntary EMG is not present, the feedback is considered reliable and the process 400 remains in closed-loop mode and proceeds to step 414.

At step 414, regardless of whether the process is in open-loop mode or closed-loop mode, the impedances of the stimulation electrodes 50, 170 are checked. At step 416, if the stimulation electrode impedances are acceptable, the process 400 proceeds to step 420 and the neurostimulator 10, 110 generates stimulation pulses, which are applied via the stimulation electrodes using the optimal electrode pattern, as determined by the nerve localization process 300 (see FIG. 7). If, at step 416, the stimulation electrode impedances are too high, the process 400 proceeds to step 420 and the neurostimulator 10, 110 generates stimulation pulses that are applied via the stimulation electrodes using an alternative electrode pattern selected from the pattern list determined by the nerve localization process 300. In either case, after generating the stimulation pulse using the optimal pattern (step 420) or the alternative pattern (step 422), the process 400 proceeds to step 424.

At step 424, the process 400 implements a pre-recording delay to allow time for the electrical stimulation applied at step 420 or 422 to elicit an EMG response. As discussed above, these delays can be relatively short, so the delay at step 424 can, likewise, be short, e.g., 5 ms or less. If the process 400 is in open loop mode, it proceeds to step 432, where a further delay is implemented. This delay 432 should match the duration of closed-loop steps 426 and 430 so that a constant stimulation period is maintained. If the process 400 is in closed-loop mode, it proceeds to step 426 and checks for feedback via the recording electrodes 60, 180. The process 400 then proceeds to step 430, where any detected EMG feedback signals are recorded and analyzed.

At this point, regardless of whether the process 400 is in open-loop mode (step 432) or closed-loop mode (step 430), the process proceeds to step 434, where a determination of whether the number of stimulation pulses applied in the current therapy session has reached a predetermined number (N). If the predetermined number (N) of pulses have not yet been applied, the process proceeds to step 436, the stimulation amplitude is maintained at the current level, and the process 400 reverts back to step 402, where the impedance of the recording electrodes is checked and the process 400 repeats. If, at step 434, the predetermined number (N) of pulses has been reached, the process 400 proceeds to step 440.

At step 440, if the process 400 in open-loop mode, the process proceeds to step 442, the stimulation amplitude is maintained at the current level, and the process 400 reverts back to step 402, where the impedance of the recording electrodes is checked and the process 400 repeats. At step 440, if the process 400 is not in open-loop mode (i.e., is in closed-loop mode), the process proceeds to step 444, where a determination is made as to whether the EMG recorded at step 430 is below a predetermined window, i.e., below a predetermined range of acceptable EMG values. If the EMG is below the predetermined window, the process 400 proceeds to step 446, where the stimulation amplitude is increased for the next pulse, if permitted. The process 400 then reverts back to step 402, where the impedance of the recording electrodes is checked and the process 400 repeats with the increased stimulation amplitude.

If, at step 444, the EMG is not below the window, the process 400 proceeds to step 450 where a determination is made as to whether the EMG is above the predetermined window. If the EMG is above the predetermined window, the process 400 proceeds to step 452, where the stimulation amplitude is decreased for the next pulse. The process 400 then reverts back to step 402, where the impedance of the recording electrodes is checked and the process 400 repeats with the decreased stimulation amplitude. If, at step 450, the EMG is not above the predetermined window, the EMG is determined to be within the predetermined window and the process 400 proceeds to step 454, where the stimulation amplitude is maintained at the current level for the next pulse. The process 400 then reverts back to step 402, where the impedance of the recording electrodes is checked and the process 400 repeats.

While aspects of this disclosure have been particularly shown and described with reference to the example aspects above, it will be understood by those of ordinary skill in the art that various additional aspects may be contemplated. A device or method incorporating any of the features described herein should be understood to fall under the scope of this disclosure as determined based upon the claims below and any equivalents thereof. Other aspects, objects, and advantages can be obtained from a study of the drawings, the disclosure, and the appended claims.

We claim:

1. A method for treating overactive bladder by applying transcutaneous electrical stimulation to the tibial nerve of a subject, comprising:
   positioning a plurality of stimulation electrodes on a skin surface at a location between the medial malleolus and the Achilles tendon proximate the tibial nerve, the stimulation electrodes being spaced from each other in a predetermined configuration;
   positioning one or more recording electrodes on a skin surface remote from the stimulation electrodes at a location on the bottom of the subject's foot near the abductor hallucis and the flexor hallucis brevis muscles to record electromyogram (EMG) responses that result from recruitment of the tibial nerve's motor fibers;
   stimulating the tibial nerve by applying electrical stimulation pulses via the plurality of stimulation electrodes according to stimulation parameters under closed-loop control in which EMG responses elicited a predetermined time after applying the electrical stimulation pulses are monitored via the recording electrodes and the stimulation parameters are adjusted in response to the monitored EMG responses; and
   in response to detecting an unacceptable condition of the recording electrodes, applying electrical stimulation pulses via the stimulation electrodes according to the stimulation parameters under open-loop control in which the stimulation parameters are maintained without adjustment.

2. The method recited in claim 1, wherein the unacceptable condition of the recording electrodes comprises an unacceptable impedance of the recording electrodes.

3. The method recited in claim 1, wherein the step of applying electrical stimulation pulses further comprises monitoring for mechanomyogram (MMG) responses to the electrical stimulation pulses and applying the electrical stimulation pulses under closed-loop control in which the stimulation parameters are adjusted in response to the monitored MMG responses.

4. The method recited in claim 1, wherein the step of applying electrical stimulation pulses comprises detecting impedances of the recording electrodes and, in response to detecting acceptable impedances of the recording electrodes, applying the electrical stimulation pulses.

5. The method recited in claim 1, further comprising:
   obtaining sample measurements via the recording electrodes;
   checking the sample measurements for noise;
   checking the sample measurements for voluntary EMG responses;
   applying the electrical stimulation pulses under closed-loop control in response to determining an acceptable level of noise and the absence of voluntary EMG responses; and
   applying the electrical stimulation pulses under open-loop control in response to determining an unacceptable level of noise or the presence of voluntary EMG responses.

6. The method recited in claim 1, wherein each application of an electrical stimulation pulse under closed-loop control comprises:
   applying the electrical stimulation pulse;
   recording, via the recording electrodes, EMG responses occurring the predetermined time after applying the electrical stimulation pulses; and
   adjusting the stimulation parameters in response to the recorded EMG responses.

7. The method recited in claim 1, wherein the duration of the predetermined time is about 5 ms or less.

8. The method recited in claim 6, wherein adjusting the stimulation parameters in response to the recorded EMG responses under closed loop control comprises:
   increasing the amplitude of subsequent stimulation pulses in response to the recorded EMG responses being below a predetermined EMG window;
   decreasing the amplitude of subsequent stimulation pulses in response to the recorded EMG responses being above the predetermined EMG window; and
   maintaining the amplitude of subsequent stimulation pulses in response to the recorded EMG responses being within the predetermined EMG window.

9. The method recited in claim 1, wherein each application of an electrical stimulation pulse under open-loop control comprises:

applying the electrical stimulation pulse; and executing a time delay having a duration sufficient to maintain a constant stimulation period.

10. The method recited in claim 9, wherein the duration of the time delay is about 75 ms.

11. The method recited in claim 1, wherein the step of stimulating the tibial nerve by applying electrical stimulation pulses via the plurality of stimulation electrodes comprises selecting a stimulation electrode pattern from a pattern list, wherein the method further comprises generating the pattern list by:

a) identifying a set of predetermined stimulation electrode patterns, each stimulation electrode pattern identifying which of the plurality of stimulation electrodes will apply the electrical stimulation pulses, and each stimulation electrode pattern having associated with it the stimulation parameters according to which it applies stimulation pulses;

b) selecting a stimulation electrode pattern from the set of predetermined stimulation electrode patterns;

c) generating a stimulation pulse using the selected stimulation electrode pattern according to its associated stimulation parameters;

d) determining via the recording electrodes whether the stimulation pulse using the selected stimulation electrode pattern elicited an EMG response;

e) adding the selected stimulation electrode pattern to the pattern list in response to detecting an EMG response;

f) omitting the selected stimulation electrode pattern from the pattern list in response to not detecting an EMG response; and repeating steps b) through f) for each stimulation electrode pattern in the set of predetermined stimulation electrode patterns to complete the pattern list.

12. The method recited in claim 11, further comprising optimizing the stimulation electrode patterns in the pattern list by:

g) adjusting the stimulation parameters for each stimulation electrode pattern in the pattern list to attempt to elicit an improved EMG response;

h) selecting a stimulation electrode pattern from the set of predetermined stimulation electrode patterns;

i) generating a stimulation pulse using the selected stimulation electrode pattern according to its associated stimulation parameters;

j) determining via the recording electrodes whether the stimulation pulse using the selected stimulation electrode pattern elicited an EMG response;

k) adding the selected stimulation electrode pattern to the pattern list in response to detecting an EMG response;

l) omitting the selected stimulation electrode pattern from the pattern list in response to not detecting an EMG response; and repeating steps h) through l) for each stimulation electrode pattern in the set of predetermined stimulation electrode patterns to complete the pattern list.

13. The method recited in claim 12, further comprising repeating steps of claim 12 until each electrode pattern in the pattern list is optimized.

14. The method recited in claim 11, further comprising ordering the stimulation electrode patterns in the pattern list according to their elicited EMG and/or MMG responses.

15. A system for treating overactive bladder by applying transcutaneous electrical stimulation to the tibial nerve of a subject, comprising:

a plurality of electrical stimulation electrodes, the stimulation electrodes being spaced from each other in a predetermined configuration;

one or more recording electrodes;

a structure for supporting the stimulation electrodes and the recording electrodes spaced apart from each other; and a control unit for controlling the operation of the stimulation electrodes and the recording electrodes, wherein the control unit is configured to perform the method of claim 1.

16. A system for treating overactive bladder by applying transcutaneous electrical stimulation to the tibial nerve of a subject, comprising:

a plurality of electrical stimulation electrodes, the stimulation electrodes being spaced from each other in a predetermined configuration;

one or more recording electrodes;

a structure for supporting the stimulation electrodes and the recording electrodes spaced apart from each other; and a control unit for controlling the operation of the stimulation electrodes and the recording electrodes, wherein the control unit is configured to perform the method of claim 11.

* * * * *